US011225502B1

(12) United States Patent
Chen

(10) Patent No.: US 11,225,502 B1
(45) Date of Patent: Jan. 18, 2022

(54) CONTROLLED SYNTHESIS OF HIERARCHICALLY-STRUCTURED HYBRID MATERIALS THROUGH PEPTOID ENGINEERING

(71) Applicant: Battelle Memorial Institute, Richland, WA (US)

(72) Inventor: Chun-Long Chen, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 16/432,710

(22) Filed: Jun. 5, 2019

Related U.S. Application Data

(60) Provisional application No. 62/683,456, filed on Jun. 11, 2018.

(51) Int. Cl.
| | |
|---|---|
| *C07K 7/02* | (2006.01) |
| *C07K 14/00* | (2006.01) |
| *C07K 1/107* | (2006.01) |
| *C07F 7/08* | (2006.01) |
| *B82Y 40/00* | (2011.01) |
| *B82Y 30/00* | (2011.01) |

(52) U.S. Cl.
CPC ............ *C07K 7/02* (2013.01); *C07F 7/087* (2013.01); *C07K 1/1077* (2013.01); *C07K 14/001* (2013.01); *B82Y 30/00* (2013.01); *B82Y 40/00* (2013.01)

(58) Field of Classification Search
None
See application file for complete search history.

(56) References Cited

U.S. PATENT DOCUMENTS

| 8,952,127 | B2 | 2/2015 | Chen et al. | |
|---|---|---|---|---|
| 9,206,233 | B2 | 12/2015 | Rosi et al. | |
| 9,764,953 | B2 | 9/2017 | Zuckermann et al. | |
| 2011/0020378 | A1* | 1/2011 | Burkhard | A61K 39/145 424/184.1 |
| 2012/0046443 | A1* | 2/2012 | Zuckermann | C07K 1/13 530/324 |
| 2012/0107242 | A1 | 5/2012 | Wang et al. | |
| 2013/0095039 | A1 | 4/2013 | Lu et al. | |
| 2016/0052969 | A1 | 2/2016 | Rosi et al. | |
| 2018/0215792 | A1 | 8/2018 | Chen | |

OTHER PUBLICATIONS

Adams et al. ('Genetically engineered peptides for inorganics:study of an unconstrained bacterial display technology and bulk aluminum alloy' Advanced Materials v25 2013 pp. 4585-4591) (Year: 2013).*
Oakley et al. ('The design of antiparallel coiled coils' Current Opinion in Structural Biology v11 2001 pp. 450-457) (Year: 2001).*
Banerjee et al., "Cu Nanocrystal Growth on Peptide Nanotubes by Biomineralization: Size Control of Cu Nanocrystals by Tuning Peptide Conformation," *Proc. Natl. Acad. Sci. U. S. A.* 2003, 100:14678-14682.
Chen et al., "Peptide-Based Methods for the Preparation of Nanostructured Inorganic Materials," *Angew Chem Int Ed.* 2010, 49:1924-1942.
Chen et al., Preparation of Unique 1-D Nanoparticle Superstructures and Tailoring their Structural Features, *J. Am. Chem. Soc.* 2010, 132(20):6902-6903.
Chen et al., "Engineered Biomimetic Polymers as Tunable Agents for Controlling $CaCO_3$ Mineralization," *Journal of the American Chemical Society,* 2011, 4 pages.
Chen et al., "Tuning calcite morphology and growth acceleration by a rational design of highly stable protein-mimetics," *Scientific Reports,* 2014, 4:6266, 11 pages.
Chiu et al., Biomolecular Specificity Controlled Nanomaterial Synthesis, Chem Soc Rev 2013, 42:2512-2527.
Dickerson et al., "Protein- and Peptide-Directed Syntheses of Inorganic Materials," *Chem. Rev.* 2008, 108:4935-4978.
Hao et al., "Synthesis and Optical Properties of "Branched" Gold Nanocrystals," *Nano Lett.* 2004, 4:327-330.
Jana et al., "Wet Chemical Synthesis of High Aspect Ratio Cylindrical Gold Nanorods," *J. Phys. Chem. B* 2001, 105:4065-4067.
Jin et al., "Highly stable and self-repairing membrane-mimetic 2D nanomaterials assembled from lipid-like Peptoids," *Nature Communications,* 2016, 7:12252, 8 pages.
Jin et al., "Designable and dynamic single-walled stiff nanotubes assembled from sequence-defined peptoids," *Nature Communications,* 2018, 9:270, 11 pages.
Katz et al., "Integrated Nanoparticle-Biomolecule Hybrid Systems: Synthesis, Properties, and Applications," *Angew. Chem., Int. Ed.* 2004, 43:6042-6108.
Lu et al., "Smart Nanomaterials Inspired by Biology: Dynamic Assembly of Error-Free Nanomaterials in Response to Multiple Chemical and Biological Stimuli," *Acc. Chem. Res.* 2007, 40:315-323.

(Continued)

*Primary Examiner* — Ronald T Niebauer
(74) *Attorney, Agent, or Firm* — Klarquist Sparkman, LLP

(57) ABSTRACT

This disclosure concerns a method for making a hybrid organic/inorganic material having an architecture. The method includes combining a peptoid comprising a sequence of N-substituted glycine residues and an inorganic material or inorganic material precursor to form a hybrid organic/inorganic material comprising the peptoid and the inorganic material, the hybrid organic/inorganic material having an architecture based at least in part on the peptoid sequence. The hybrid organic/inorganic materials include a cluster of nanoparticles of an inorganic material and peptoids, the cluster formed by random attachment of nanoparticles to one another by peptoid-peptoid and peptoid-nanoparticle surface interactions, wherein the hybrid material has an architecture based at least in part on the peptoid sequence.

14 Claims, 14 Drawing Sheets

(13 of 14 Drawing Sheet(s) Filed in Color)

(56) References Cited

OTHER PUBLICATIONS

Ma et al., "Tuning crystallization pathways through sequence engineering of biomimetic polymers," *Nature Materials,* 2017, 16:767-775.
Mannige et al., "Peptoid nanosheets exhibit a new secondary-structure motif," *Letter,* 2015, 526:415-422.
Meldrum et al., "Controlling Mineral Morphologies and Structures in Biological and Synthetic Systems," Chem Rev 2008, 108:4332-4432.
Naik et al., "Biomimetic Synthesis and Patterning of Silver Nanoparticles," *Nat. Mater.* 2002, 1:169-172.
Slocik et al., "Sequenced Defined Biomolecules for Nanomaterial Synthesis, Functionalization, and Assembly," Curr Opin Biotechnol 2017, 46:7-13.
Sun et al., "Shape-Controlled Synthesis of Gold and Silver Nanoparticles," *Science* 2002, 298:2176-2179.
Tao et al., "Shape Control of Colloidal Metal Nanocrystals," *Small* 2008, 4:310-325.
Tigger-Zaborov et al., "Nanoparticles assemblies on demand: Controlled aggregation of Ag(0) mediated by modified peptoid sequences," *Journal of Colloid and Interface Science,* 2017, 508:56-64.
Tigger-Zaborov et al., "Aggregation of Ag(0) nanoparticles to unexpected stable chainlike assemblies mediated by 2,2'-bipyridine decorated peptoids," *Journal of Colloid and Interface Science,* 2019, 533:598-603.
Xia et al., Shape-Controlled Synthesis of Metal Nanocrystals: Simple Chemistry Meets Complex Physics? *Angew. Chem., Int. Ed.* 2009, 48:60-103.
Yan et al., "Controlled synthesis of highly-branched plasmonic gold nanoparticles through peptoid engineering," *Nature Communications,* 2018, 9:2327 8 pages.

\* cited by examiner

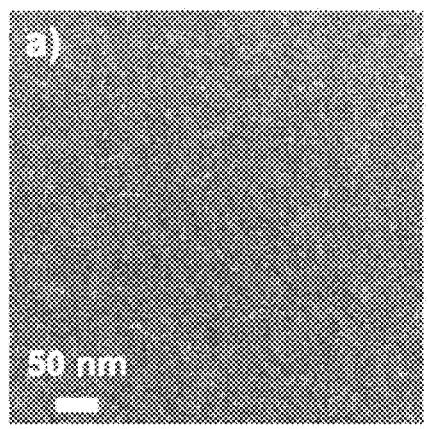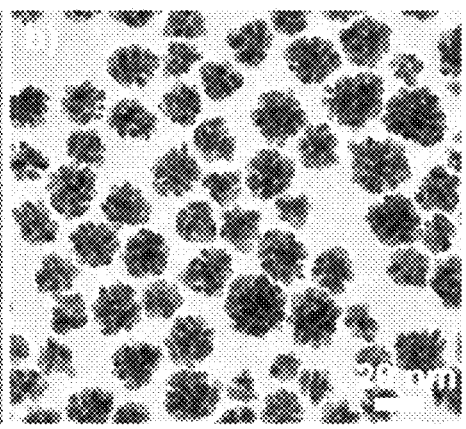
FIG. 10    FIG. 11
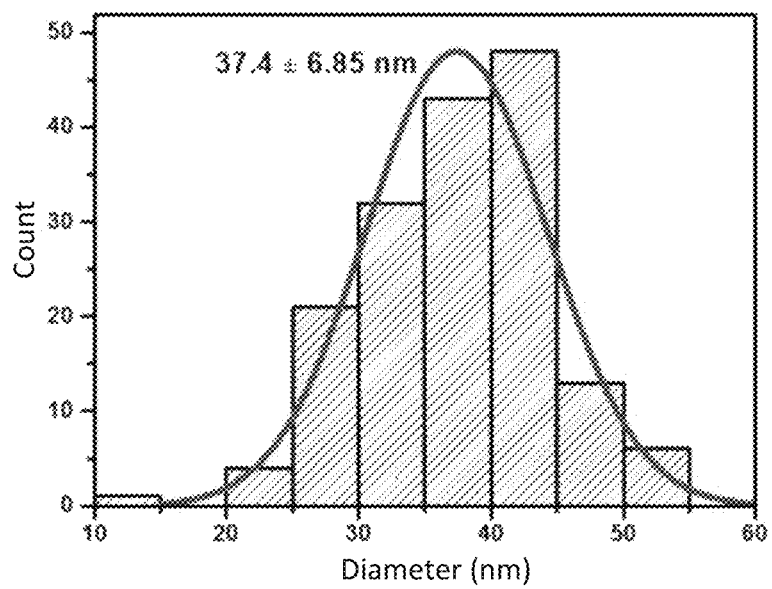
FIG. 12
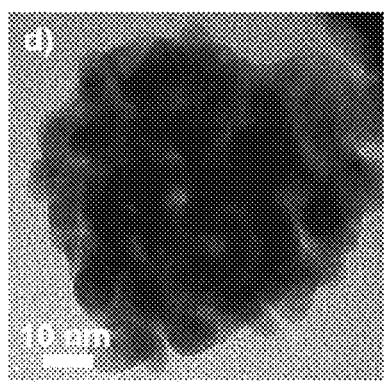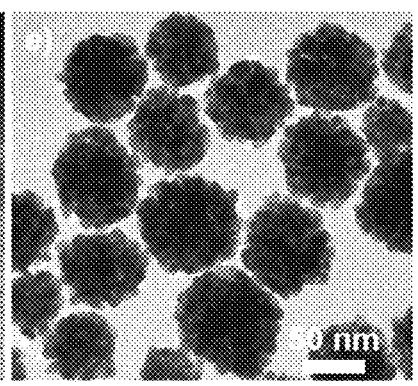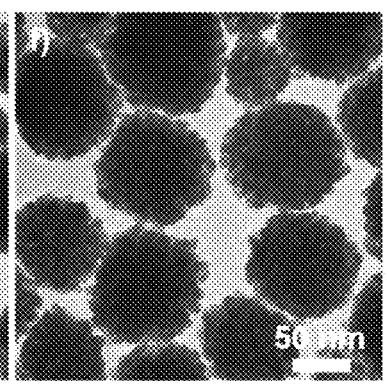
FIG. 13    FIG. 14    FIG. 15

FIG. 16A  FIG. 16B  FIG. 16C
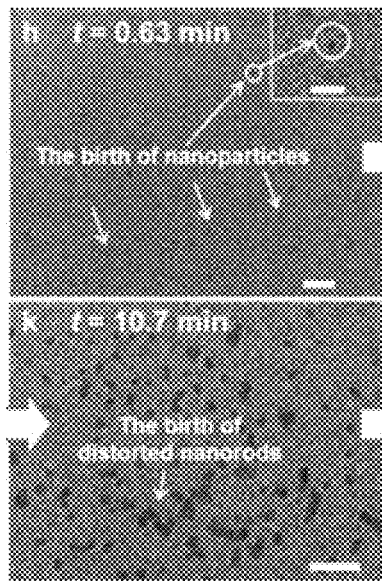 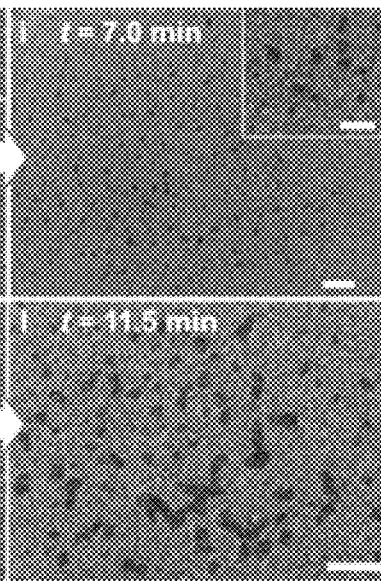 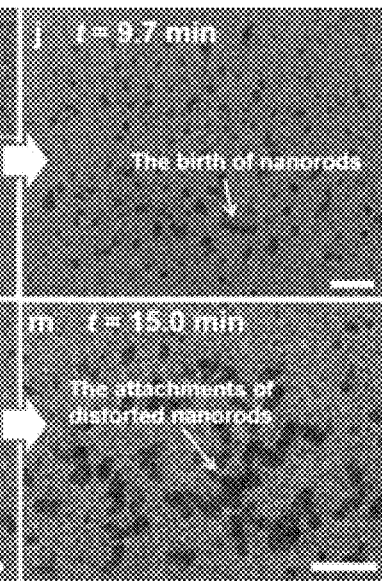
FIG. 16D  FIG. 16E  FIG. 16F
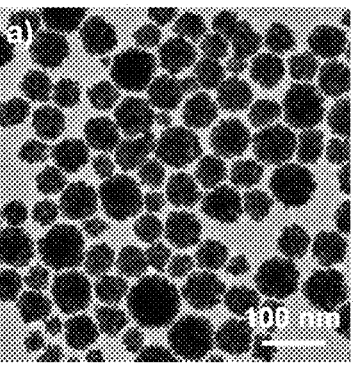
FIG. 17
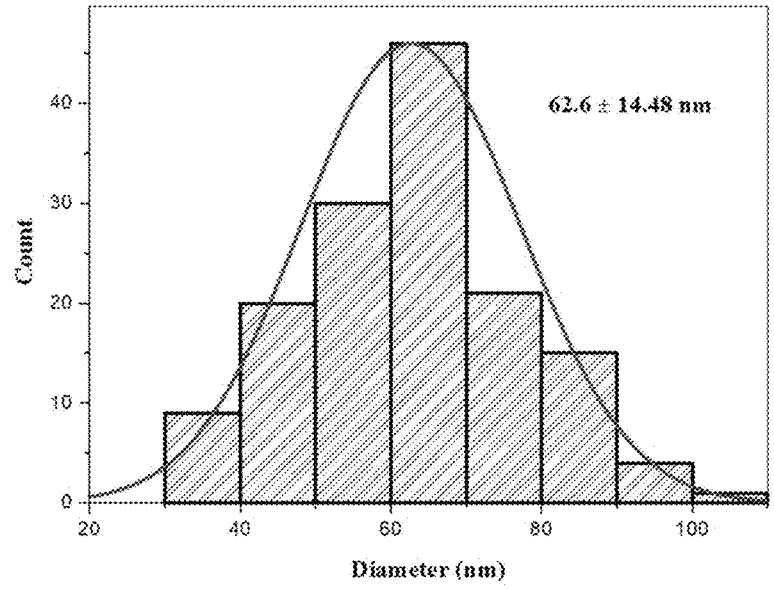
FIG. 18

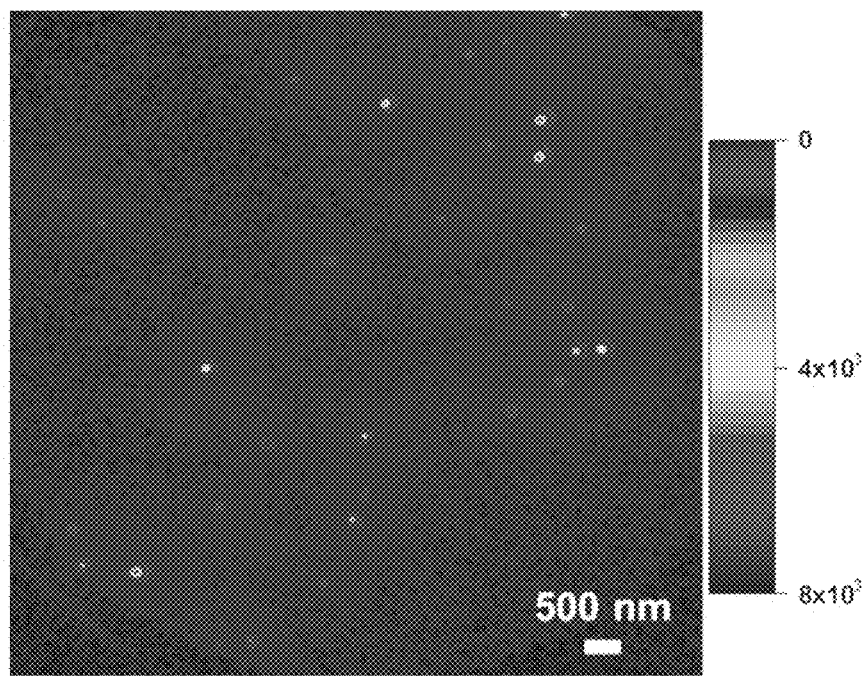
FIG. 48
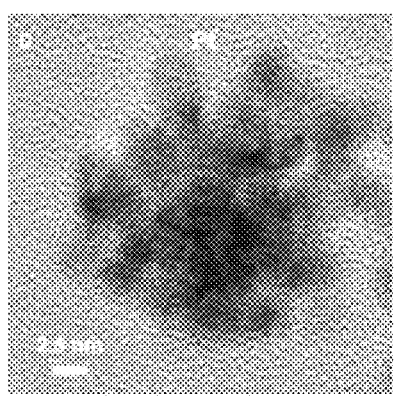 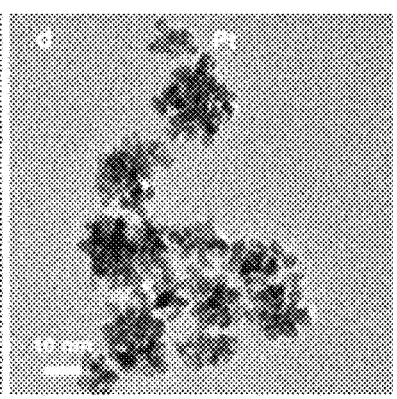 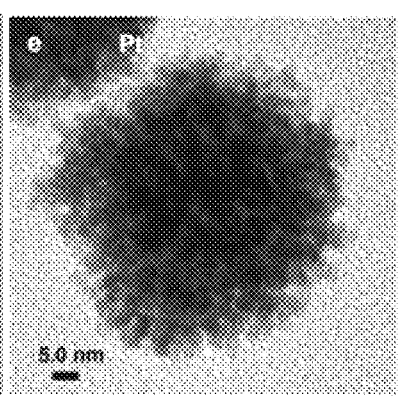
FIG. 49A　　　　FIG. 49B　　　　FIG. 50A
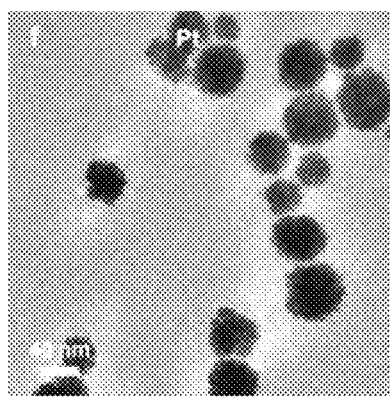 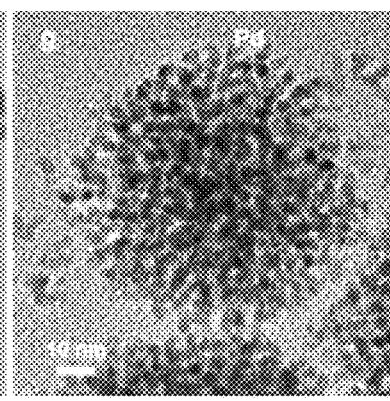 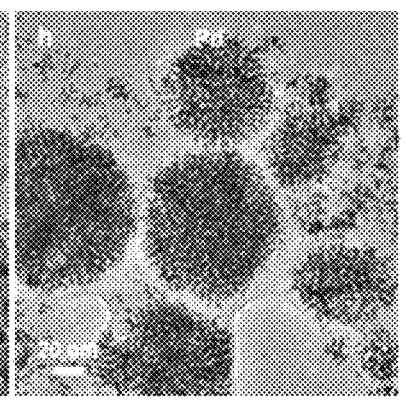
FIG. 50B　　　　FIG. 51A　　　　FIG. 51B

CONTROLLED SYNTHESIS OF HIERARCHICALLY-STRUCTURED HYBRID MATERIALS THROUGH PEPTOID ENGINEERING

CROSS REFERENCE TO RELATED APPLICATION

This application claims the benefit of the earlier filing date of U.S. Provisional Application No. 62/683,456, filed Jun. 11, 2018, which is incorporated by reference herein in its entirety.

ACKNOWLEDGMENT OF GOVERNMENT SUPPORT

This invention was made with Government support under Contract DE-AC05-76RL01830 awarded by the U.S. Department of Energy. The Government has certain rights in the invention.

FIELD

This disclosure concerns embodiments of a method for using peptoids to synthesize hybrid organic/inorganic materials having a desired architecture, as well as materials made by the disclosed methods.

BACKGROUND

Natural organisms produce a wide variety of exquisitely complex, nano-, micro-, and macroscale functional materials at high yields in an energy-efficient and highly reproducible manner. Throughout these processes (which generally take place in rather mild typically aqueous conditions) specialized proteins and peptides are produced. These complex materials may be responsible for any of a variety of activities including crystal nucleation, growth kinetics, phase and architecture, ultimately giving rise to biominerals with versatile functions. Inspired by nature, various attempts have been made to create similar structures through various processes. These approaches are attractive because they generate complex, functional nanomaterials under mild conditions. Furthermore, materials made by the unique integration of bio-and inorganic nanomaterials have demonstrated superior performance.

Despite these advances, development of methods based upon these design principles remain elusive. A variety of factors including the complex folding of proteins and peptides make the prediction of their functions rather difficult. Furthermore, although proteins and peptides can provide improved solubility, biocompatibility and bio-targeting to inorganic nanomaterials, they are often problematic for applications due to their poor thermal and chemical stabilities. To overcome these challenges, methods for producing biomimetic systems are needed that can confer a similar level of molecular recognition and possess a higher stability, while also featuring greater simplicity in terms of tuning their functions.

SUMMARY

Embodiments of a method for producing a hybrid organic/inorganic material having an architecture include combining (i) a peptoid comprising a sequence of N-substituted glycine residues and (ii) an inorganic material or inorganic material precursor to form the peptoid and the inorganic material or inorganic material precursor into a hybrid organic/inorganic material comprising the peptoid and the inorganic material, the hybrid organic-inorganic material having an architecture based at least in part on the sequence of N-substituted glycine residues in the peptoid. As used herein, the term "inorganic material" may refer to a material that is solely inorganic or a material that is an inorganic-organic material (e.g., a silicon-organic material). In some examples, the hybrid organic-inorganic material comprises a plurality of distorted nanorods and a plurality of peptoids, wherein at least some of the peptoids are adsorbed to surfaces of the distorted nanorods, the plurality of distorted nanorods being randomly attached together via peptoid-peptoid and peptoid-nanorod interactions. In some embodiments, the architecture is an ordered three-dimensional structure. In certain embodiments, the architecture is spherical, dendritic, spherical dendritic, or a nanotube.

In some embodiments, the peptoid comprises residues with side-chains derived from 1,4-butanediamine, aminoethanol, ethylamine, β-alanine, 4-aminobutyramide, phenethylamine, halogen-substituted phenethylamine, and tyramine to mimic related amino acids. For example, N-(2-carboxyethyl)glycine (Nce) side chain was derived from β-alanine to mimic aspartic or glutamic acid, N-(4-aminobutyl)glycine (Nab) was derived from 1,4-butanediamine to mimic lysine, side chain N-[2-(4-X-phenyl)ethyl]glycine (Nxpe) where X is H or halogen was derived from phenethylamine or halogen substituted phenethylamine to mimic phenylalanine. In any of the foregoing embodiments, the inorganic material may comprise Au, Pd, Pt, Ag, $TiO_2$, iron oxide, a silica, or any combination thereof. In an independent embodiment, the inorganic-organic material is a polyhedral oligomeric silsesquioxane (POS).

In any of the foregoing embodiments, the method may further include combining the peptoid and an inorganic material precursor with a solvent to provide a solution; adding a reducing agent to the solution; and allowing a reaction to occur for a period of time effective to provide reduction of the inorganic material precursor to form inorganic material nanoparticles, subsequent merging of nanoparticles to form larger particles, and adsorption of peptoids to surfaces of the particles, thereby randomly attaching particles to each other and forming particle clusters. In some embodiments, the subsequent merging of the nanoparticles forms nanorods. Adsorption of the peptoids to the surfaces of the nanorods and peptoid-peptoid interactions randomly attaches nanorods to each other, thereby forming nanorod clusters. In certain embodiments, the reducing agent comprises 4-(2-hydroxyethyl)-1-piperazineethanesulfonic acid, ascorbic acid or a combination thereof; and the inorganic material precursor comprises chloroauric acid, potassium tetrachloroplatinate (II), sodium tetrachloropalladate (II), or a combination thereof.

This disclosure also includes hybrid organic/inorganic materials made by embodiments of the disclosed method. The hybrid organic/inorganic material comprises a plurality of peptoids, each peptoid having a sequence of N-substituted glycine residues, and an inorganic material, wherein the hybrid organic/inorganic material comprises a plurality of nanoparticles comprising the inorganic material, the nanoparticles are randomly attached together via the plurality of peptoids thereby forming a cluster of nanoparticles joined by peptoids, and the hybrid organic/inorganic material has an architecture based at least in part on the sequence of N-substituted glycine residues in the peptoids.

In some embodiments, the inorganic material comprises Au, Pd, Pt, or any combination thereof. In certain such embodiments, (i) the sequence of N-substituted glycine residues includes an N-terminal group of at least four sequential Ndc residues, at least one Nce residue, and at least one Nab or Nae residue; or (ii) the nanoparticles are nanorods, such as distorted nanorods; or (iii) the architecture is dendritic or spherical dendritic; or (iv) any combination of (i), (ii), and (iii). In any of the foregoing embodiments, particles of the hybrid organic/inorganic material may have a plasmonic enhancement of up to $10^5$.

The foregoing and other objects, features, and advantages of the invention will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 10 is a negatively-stained TEM image showing that no ordered Pep-1 assemblies were formed in early stages of the nanomaterial formation; scale bar=50 nm; 2% phosphotungstic acid was used for negative staining.

FIG. 11 is a TEM image showing nanoparticles of Pep-1/gold nanomaterial formed at 60° C.; scale bar=20 nm.

FIG. 12 is a graph showing the size distribution of the nanoparticles of FIG. 11.

FIG. 13 is a TEM image showing nanoparticles of Pep-1/gold nanomaterial formed under continuously stirring conditions; scale bar=10 nm.

FIG. 14 is a TEM image showing nanoparticles of Pep-1/gold nanomaterial after incubation at 60° C. in water for 30 hours; scale bar=50 nm.

FIG. 15 is a TEM image showing nanoparticles of Pep-1/gold nanomaterial after incubation in 1.0 M aqueous NaCl for 5 days.

FIGS. 16A-16F are a time series of in situ liquid TEM images (scale bar, 20 nm) showing the birth of gold nanoparticles (16A, 16B), nanorods (16C), distorted nanorods (16D), and clusters of distorted nanorods (16E, 16F) during early stages of coral-shaped particle formation; top right corner insets of 16A and 16B are high-magnification TEM images showing gold nanoparticles (scale bar, 10 nm).

FIG. 17 is a TEM image showing nanoparticles of Pep-2/gold nanomaterial; scale bar, 100 nm.

FIG. 18 is a graph showing the size distribution of the nanoparticles of FIG. 17.

FIG. 48 is a TP-PEEM of a sparse distribution of particles showing the photoemission enhancement map (scale bar=500 nm) of Pep-5/gold nanoparticles with a strongest plasmonic enhancement of about 103.

FIGS. 49A and 49B are TEM images showing nanoparticles of Pep-1/Pt nanomaterial produced by reduction of $Pt^{2+}$ cations by HEPES buffer and ascorbic acid at 35° C.; scale bar=2.5 nm (49A), 10 nm (49B).

FIGS. 50A and 50B are TEM images showing nanoparticles of Pep-1/Pt nanomaterial produced by reduction of $Pt^{2+}$ cations by ascorbic acid at 35° C.; scale bar=5.0 nm (50A), 40 nm (50B).

FIGS. 51A and 51B are TEM images showing nanoparticles of Pep-1/Pd nanomaterial produced by reduction of $Pd^{2+}$ cations by ascorbic acid at 35° C.; scale bar=10 nm (51A), 20 nm (51B).

DETAILED DESCRIPTION

Figure 1:
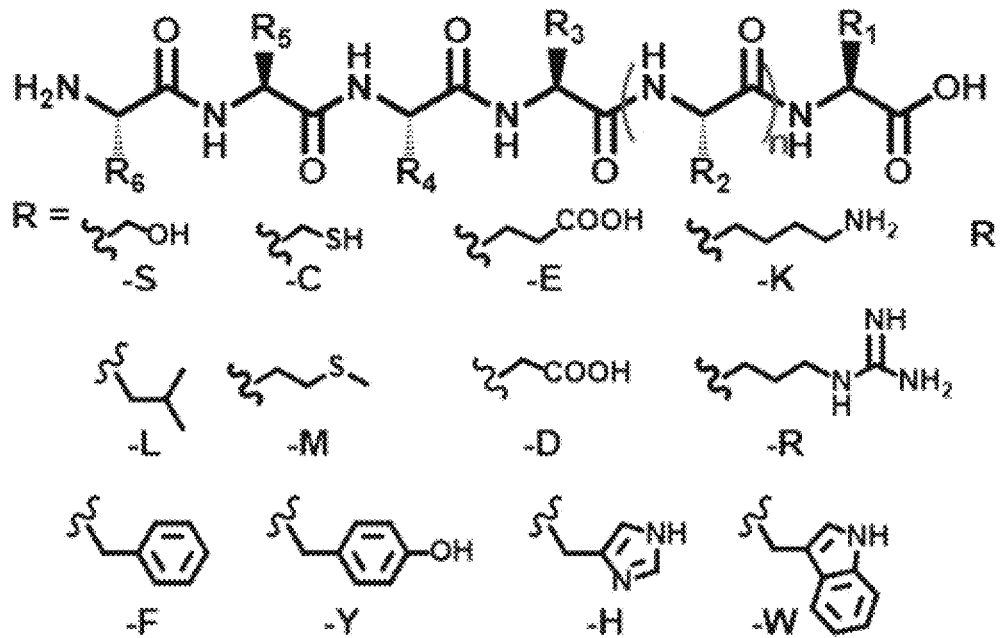
FIG. 1 shows exemplary peptoids to mimic related peptides with similar side chain chemistries.
Figure 1:
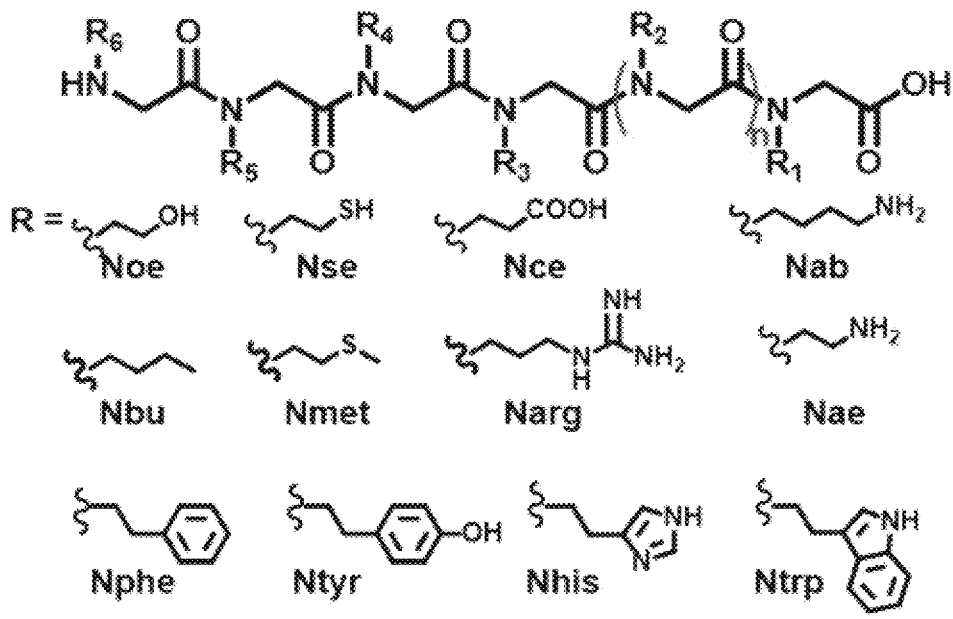

This disclosure concerns the design of peptoids that lead to the controlled synthesis of hierarchically-structured hybrid materials, including the highly-branched plasmonic hybrid organic/inorganic nanoparticles. By preparing peptoids with specific arrangements, or sequences, of N-substituted glycine residues, synthesis of hybrid materials with hierarchical architecture is performed. In some embodiments, individual spherical dendritic (coral-shaped) nanoparticles exhibit a plasmonic enhancement as high as $10^5$ fold compared to simple spherical nanoparticles. This disclosure provides a significant advance toward the ultimate vision of predictive bio-inspired materials synthesis using sequence-defined synthetic molecules that mimic proteins and peptides. Embodiments of the hybrid organic/inorganic materials combine the functionality of inorganic nanomaterials with the ability of macromolecules to form ordered 3D structures.

Embodiments of the disclosed method provide model systems for understanding biocontrolled crystallization mechanisms. Moreover, in some embodiments, the resulting nanomaterials are biocompatible and exhibit unique optical and electronic properties (e.g., plasmonics) that can be used for chemical and biological imaging applications.

I. DEFINITIONS AND ABBREVIATIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

The disclosure of numerical ranges should be understood as referring to each discrete point within the range, inclusive of endpoints, unless otherwise noted. Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Although there are alternatives for various components, parameters, operating conditions, etc. set forth herein, that does not mean that those alternatives are necessarily equivalent and/or perform equally well. Nor does it mean that the alternatives are listed in a preferred order unless stated otherwise.

Definitions of common terms in chemistry may be found in Richard J. Lewis, Sr. (ed.), *Hawley's Condensed Chemical Dictionary*, published by John Wiley & Sons, Inc., 2016 (ISBN 978-1-118-13515-0).

In order to facilitate review of the various embodiments of the disclosure, the following explanations of specific terms are provided:

Adsorption/adsorbed: The immediate physical contact with or bonding of ions and molecules onto the surface of another molecule. An ion or molecule that adsorbs is referred to as an adsorbate. Adsorption can be characterized as chemisorption or physisorption, depending on the character and strength of the bond between the adsorbate and the substrate surface.

Architecture: A designed structure. As used herein, the term "architecture" refers to the shape and configuration of particles of the hybrid organic/inorganic materials. The terms "architecture" and "morphology" may be used interchangeably herein.

Attached: The term "attached" as used herein, with respect to the attachment of peptoid-stabilized particles, refers to the joining of two or more particles by means of peptoid-peptoid and peptoid-particle surface interactions. Peptoid-peptoid interactions occur among side chains and include hydrogen bonds, coordination bonds, and/or hydrophobic interactions. As additional inorganic material subsequently is deposited onto the first and second particles, portions of the peptoid molecules may subsequently become partially or completely embedded within the inorganic material.

Dendritic: Having a branched form, e.g., resembling a tree or a branched coral.

Distorted: Twisted out of shape, irregular. For example, as used herein, the term "distorted nanorod" refers to a nanorod that does not appear to have a constant diameter along its length and/or does not necessarily have a right cylindrical shape (with flat or rounded ends) when viewed with a transmission electron microscope (TEM). In other words, when viewed with a TEM, the distorted nanorod has a bumpy surface and/or is bent.

Hybrid: As used herein, the term "hybrid" refers to a material including an organic component (e.g., a peptoid) and an inorganic component, e.g., a metal, an oxide, or a polyhedral oligomeric silsesquioxane.

Inorganic material precursor: As used herein, the term "inorganic material precursor" refers to a compound that participates in a chemical reaction to form the inorganic material. When the inorganic material is a metal, the precursor may include cations of the inorganic material. As one example, gold cations in chlorauric acid (inorganic material precursor) may be reduced to form gold (inorganic material).

Merge: As used here, the term "merge" refers to a plurality of nanoparticles joining to form a larger nanoparticle. For example, in the presence of certain peptoids, a plurality of metal nanoparticles may merge via particle-particle interactions, resulting from dissolution and nucleation processes, to form a nanorod structure.

Nanoparticle: A nanoscale particle with a size that is measured in nanometers, for example, a nanoscopic particle that has at least one dimension of ≤200 nm, such as ≤100 nm. Nanoparticles may have a size range of from 5 to 200 nm, such as from 10 to 200 nm, or 10 to 100 nm As used herein, a nanoparticle may be a metal nanoparticle, a metal oxide nanoparticle, a silica nanoparticle, or a hybrid organic/inorganic nanoparticle comprising one or more peptoids and an inorganic material (e.g., a metal, a metal oxide, a silica).

Nanorod: A nanoparticle having an elongated rod-like structure. In some embodiments, a nanorod may have an aspect ratio (length/width) within a range of 3-10.

Nanotube: A nanoscale tube-like structure with an open interior space.

Ordered: Characterized by regularity. For example, when viewed with a TEM, an ordered nanotube may have an apparently smooth surface and/or a constant diameter along its length.

Peptoid: A poly-N-substituted glycine. Peptoids are a class peptidomimetics whose side-chains are attached to the nitrogen of the oligomer backbone rather than to the $\alpha$-carbon as in peptides. Peptoids lack the amide hydrogen, which is responsible for many of the secondary structure features of peptides.

Peptoid-stabilized particle: A particle with one or more peptoid molecules adsorbed to the particle surface.

Polyhedral oligomeric silsesquioxane (POS): An organosilicon oligomer formed from monomers having the formula $R'SiO_{1.5}$ where R' is H, aliphatic, aryl, or alkoxy. A POS molecule is a hybrid intermediate between silica ($SiO_2$) and silicone ($R'_2SiO$) and has a formula $[R'SiO_{1.5}]_m$ where m is an integer ≥6. Silsesquioxanes form cage-like polymeric structures with Si-O-Si bonds and tetrahedral Si vertices. The structure has a silica-like core surrounded by a shell of organic groups.

POS Nanocluster: As used herein, the term "POS nanocluster" refers to a polyhedral oligomeric silsesquioxane particle having a cage-like polymeric structure.

Residue: A monomeric unit of a peptoid, —N(R)—$CH_2$C(O)—, where R is a side chain.

Sequence: As used herein, the term "sequence" refers to a specific arrangement (identity and placement) of residues or side chains in the peptoid molecule.

Spherical dendritic: A dendritic particle with branches generally extending outwardly from a core of the particle thereby giving the dendritic particle a generally spherical shape. Also referred to as a spherical coral shape.

II. METHOD OF MAKING HYBRID ORGANIC/INORGANIC MATERIALS

Peptoids with a specific sequence of side chains are used to prepare hybrid organic/inorganic materials with desired architectures, wherein the architecture is based at least in part on peptoid sequence. As used herein, the terms "architecture" and "morphology" are used interchangeably to describe the shape of the hybrid materials. The peptoids have preselected characteristics including side chains with desired activity and/or characteristics such as charge or neutrality, hydrophobicity or hydrophilicity, attraction or repulsion toward preselected materials or functional groups, and combinations thereof. The arrangement of peptoid side chain residues influences the architecture of the resulting hybrid materials. For instance, in some examples, preselected criteria included presence of amino-containing and/or carboxyl-containing side chains, presence of residues with strong hydrophobicity, and specific arrangements of such residues. Combining the preselected peptoids with particular inorganic materials under effective conditions leads to hybrid organic/inorganic materials with architectures predicted by the peptoid sequences, inorganic materials, and selected reaction conditions.

Peptoids offer unique advantages for controlled synthesis of particles with desired morphologies compared to other sequence-defined molecules such as peptides and oligonucleotides. These advantages include a lack of backbone hydrogen bonding, a wide variety of potential side chains with varying properties, and/or greater chemical and/or thermal stabilities compared to peptides and oligonucleotides. The lack of backbone hydrogen bond donors allows explicit introduction of peptoid-peptoid and peptoid-surface interactions through the side chains. Peptoid-peptoid interactions include intermolecular attractive forces such as hydrogen bonds, coordination bonds, and/or hydrophobic interactions. Peptoid-surface interactions occur when a peptoid is adsorbed to a particle surface. Peptoids are biocompatible, highly stable, and offer peptide- and protein-like molecular recognition. Additionally, peptoids can be cheaply and efficiently synthesized through a sub-monomer synthetic method with many commercially available moieties that can be used to attain side-chain diversity.

FIG. 1 shows exemplary peptoids to mimic related peptides with similar side chain (R) chemistries.

Most, if not all, amino acids can be represented by one or more analogous N-substituted glycine monomers. Some peptoid side chains are synthesized using primary amines. For example, a side chain derived from 1,4-butanediamine is used to mimic lysine, aminoethanol is used to mimic serine and threonine, ethylamine is used to mimic alanine. Additionally, β-alanine (3-aminopropanoic acid), 1,4-butanediamine, and 4-aminobutyramide are used to mimic glutamine. β-alanine also can be used to mimic aspartic or glutamic acids, tyramine can be used to mimic tyrosine, and phenethylamine or substituted phenethylamine can be used to mimic phenylalanine. Side-chain diversity and side-chain variations are significant for controlling inorganic crystal formation and subsequent architecture.

Exemplary peptoid side chains (R) include, but are not limited to, —$(CH_2)_2OH$, —$(CH_2)_2SH$, —$CH_2COOH$, —$(CH_2)_2COOH$, —$(CH_2)_4NH_2$, —$(CH_2)_4$, —$(CH_2)_2SCH_3$, —$(CH_2)_3N(H)C(=NH)NH_2$, —$(CH_2)_2NH_2$,

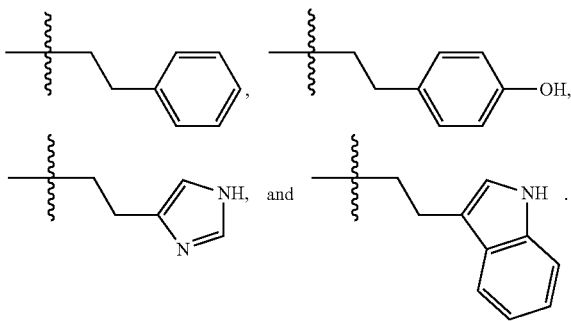

In some embodiments, the peptoid comprises a specific arrangement of N-substituted glycine residues and has a general structure:

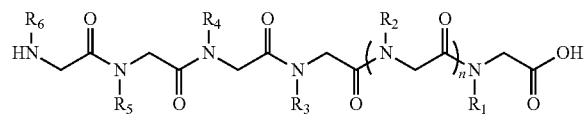

where $R_1$-$R_6$ individually are side chains as disclosed above and n is an integer from 1 to 45, such as from 3 to 45, 3 to 35, 3 to 25, or 3 to 15.

In some embodiments, the peptoids include residues selected from N-(2-carboxyethyl)glycine (Nce), N-(4-aminobutyl)glycine (Nab), N-[2-(4-X-phenyl)ethyl]glycine (Nxpe) where X is H or halo, N-[2-(2,4-dichlorophenyl) ethyl]glycine (Ndc), N-(4-aminoethyl)glycine (Nae), and combinations thereof. The peptoids additionally may include other side chains as described above. Nce is a hydrophilic monomer that can mimic aspartic or glutamic amino acids. Nab and Nae are also hydrophilic and have properties similar to lysine. Nxpe residues are hydrophobic and can mimic hydrophobic amino acids, such as phenylalanine. Exemplary residues include, but are not limited to:

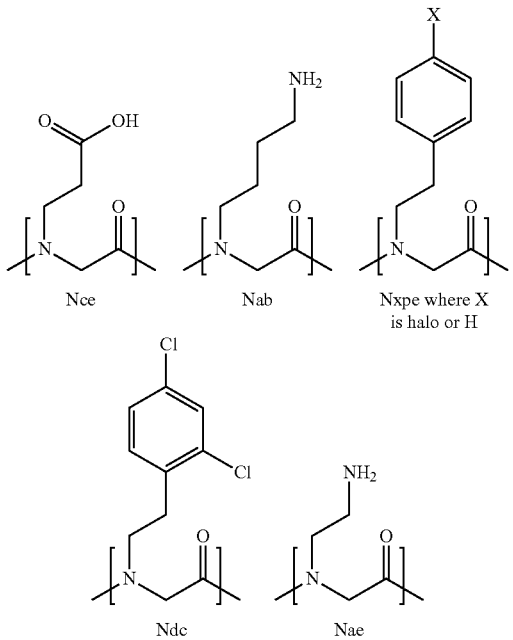

Embodiments of the disclosed peptoids may include residues derived from at least 6 monomers, at least 8 monomers, at least 10 monomers, or at least 12 monomers, as disclosed herein. In some embodiments, the disclosed peptoids include at least 6 N-substituted glycine residues, at least 8 N-substituted glycine residues, at least 10 N-substituted glycine residues, or at least 12 N-substituted glycine residues. In some embodiments, the peptoids include from 6-50, 8-50, 8-40, 8-30, or 8-20 residues as disclosed herein, such as from 6-50, 8-50, 8-40, 8-30, or 8-20 N-substituted glycine residues. The peptoid may include a series of groups of particular residues, such as groups including at least three or at least four of a single residue, e.g., a group of 4 Nce or Ndc residues. In some examples, the peptoids may include groups of 4-12 residues of a single residue, such as 4-12 residues of a single N-substituted glycine.

Exemplary peptoids include, but are not limited to:
Pep-1—$(Nce)_8(Nab)_4(Ndc)_4$
Pep-2—$(Nce)_{12}(Nab)_4(Ndc)_4$
Pep-3—$(Nce)_4(Nab)_4(Ndc)_4$
Pep-4—$(Nce)_8(Nab)_4(Nxpe)_4$ where X is Cl
Pep-5—$(Nce)_8(Nab)_4(Npe)_4$
Pep-6—$(Nce)_8(Ndc)_4$
Pep-7—$(Nce)_8(Nae)_4(Ndc)_4$
Pep-8—$(Nce)_8(Nab)(Ndc)_4$
Pep-9—$(Nce)_4(Ndc)_4(Nab)_4$
Pep-10—$(Nce)_{12}(Ndc)_4(Nab)_4$
Pep-11—$(Nce)_8(Nab)_4(Nxpe)_4$ where X is Br Embodiments of the disclosed hybrid organic/inorganic materials include peptoids and an inorganic material. As used herein, the term "inorganic material" may refer to a material that is solely inorganic or a material that is an inorganic-organic material (e.g., a silicon-organic material). In some embodiments, the inorganic material comprises a metal. In certain embodiments, the inorganic material is a metal in its elemental state. In some examples, the metal is a transition metal. The metal may be a metal that is biologically inert, and does not cause adverse effects when administered to a subject, such as a human or non-human mammal. Non-limiting examples of suitable metals include Au, Pd, Pt, and Ag.

In some embodiments, the inorganic material comprises an oxide, such as a metal oxide or a silica. The oxide may be biologically inert and without adverse effects when administered to a subject. Non-limiting examples of suitable oxides include $TiO_2$, iron oxide (FeO or $Fe_2O_3$), and silicas.

In certain embodiments, the inorganic material may be an inorganic-organic material, such as a polyhedral oligomeric silsesquioxane (POS). A silsesquioxane is an oligomeric organosilicon compound having the formula $[R'SiO_{1.5}]_m$ where each R' independently is H, aliphatic, aryl, or alkoxy, and m is an integer ≥6. Silsesquioxanes form cage-like polymeric structures with Si-O-Si bonds and tetrahedral Si vertices. The structure has a silica-like core surrounded by a shell of organic groups. An exemplary POS structure is shown below:

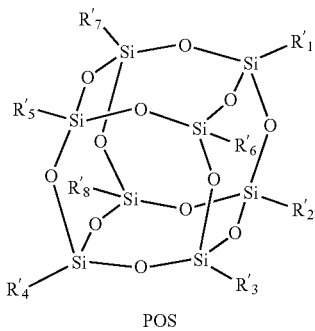

POS

A preselected peptoid is combined with an inorganic material or an inorganic material precursor to assemble the peptoid and the inorganic material or inorganic material precursor into a hybrid organic/inorganic material comprising the peptoid and the inorganic material, the hybrid organic/inorganic material having an architecture based at least in part on the sequence of residues in the peptoid. Thus, the peptoid sequence may be selected based at least in part upon a desired architecture for the hybrid organic/inorganic material.

In some embodiments, combining the peptoid and the inorganic material or inorganic material precursor to assemble the peptoid and the inorganic material into the hybrid organic/inorganic material includes combining the peptoid and an inorganic material precursor (e.g., a salt or acid of the inorganic material) comprising cations of the inorganic material with a solvent to provide a solution, adding a reducing agent to the solution, and allowing a reaction to occur for a period of time effective to provide reduction of the inorganic material cations to form inorganic material nanoparticles, subsequent merging of nanoparticles to form larger particles, and adsorption of peptoids to surfaces of the particles, thereby randomly attaching particles to each other and forming particle clusters via peptoid-peptoid and peptoid-surface interactions. In an independent embodiment when the inorganic material is an oxide, the conditions may be hydrolysis conditions, and a reducing agent is not included; for example, when the inorganic material precursor is tetraethylorthosilicate (TEOS), the reaction may be peptoid hydrolysis of TEOS to investigate peptoid-controlled silicification. The solution may be left to stand undisturbed during the effective period of time. Alternatively, the solution may be intermittently or continuously mixed during the effective period of time. In some embodiments, the effective period of time is from 2-75 hours, such as from 5-75 hours or 5-60 hours.

Figure 2:
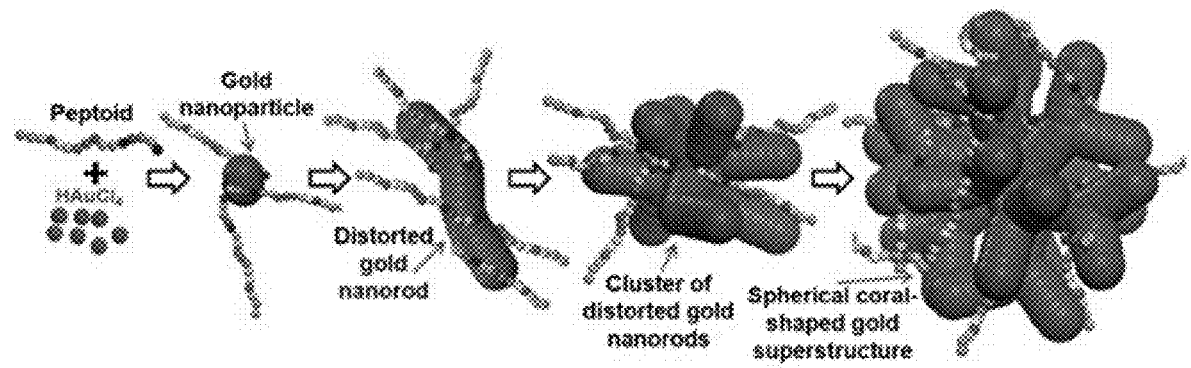
FIG. 2 is a schematic diagram showing a proposed mechanism for formation of some embodiments of the disclosed hybrid organic/inorganic nanomaterials.
Figure 5:
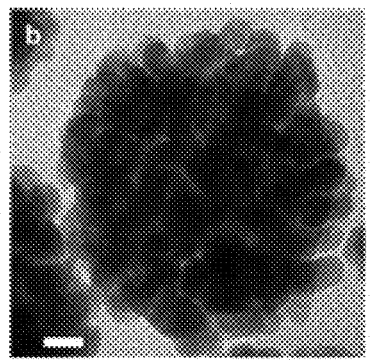
FIG. 5 is a TEM image of a single nanoparticle of the Pep-1/gold nanomaterial; scale bar=10 nm.
Figure 7:
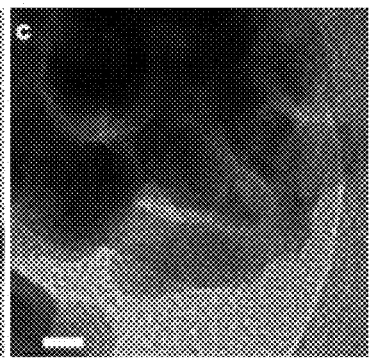
FIG. 7 is a high-resolution TEM (HR-TEM) image of a portion of a single nanoparticle of the Pep-1/gold nanomaterial; scale bar=5 nm.
Figure 9A:
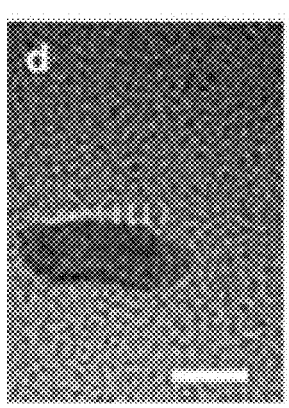
FIGS. 9A-9D are HR-TEM images of distorted gold nanorods with (111) lattice fringes (9A) and clusters of the nanorods exhibiting both (111) and (200) fringes formed in early stages of the Pep-1/gold nanomaterial formation (9B-9D); scale bar=5.0 nm.

In certain embodiments (e.g., as shown in FIG. 2), the inorganic material nanoparticles merge to form inorganic material nanorods. The nanorods then form nanorod clusters through a non-orientated attachment process due to adsorption of peptoids to surfaces of the nanorods and peptoid hydrophobicity, thereby providing peptoid-surface and peptoid-peptoid interactions. The nanorods may be "distorted" nanorods. As used herein, "distorted" means that the nanorod does not appear to have a constant diameter along its length and/or the nanorod does not necessarily have a right cylindrical shape (with flat or rounded ends) when viewed with a transmission electron microscope (TEM). In other words, when viewed with a TEM, the nanorods have a bumpy surface and/or are bent (see, e.g., FIGS. 5, 7, 9A). In some embodiments, the nanorods have an average diameter of ≤25 nm, such as ≤20 nm, ≤15 nm, or ≤10 nm. As used herein, "average diameter" means the mathematical average diameter of a plurality of nanorods. In certain embodiments, the nanorods have an average diameter of 2-25 nm, 5-25 nm, 5-20 nm, 5-15 nm, or 5-10 nm.

In some embodiments, the period of time may be effective to further provide additional deposition of nanoparticles onto the larger particles or nanorods. Additional deposition may result in at least a portion of one or more peptoids being embedded within the larger particle or nanorod as it grows.

The solvent used for the formation of the hybrid materials is an aqueous solvent, such as an aqueous buffer. In one embodiment, the solvent is a 4-(2-hydroxyethyl)-1-piperazineethanesulfonic acid (HEPES) buffer. The HEPES also serves as a weak capping and mild reducing agent as discussed below. In some embodiments, the solution has a pH≥5.5, such as a pH≥7, ≥8, ≥9, or even ≥10. The pH may be, for example, within a range of 5.5-12, such as a pH of 7-12. In certain embodiments, the pH is selected such that carboxyl groups on the peptoid are deprotonated. For example, at pH≥7.3 all carboxyl groups may be deprotonated, providing greater adsorption of the peptoid to gold surfaces through electronic interactions. In some embodiments, the pH may affect the subsequent architecture and/or size of the inorganic material nanoparticles and/or the resulting hybrid organic/inorganic material.

In some embodiments, the inorganic material precursor is an acid or an aqueous soluble salt comprising cations of the inorganic material. Exemplary precursors include, but are not limited to, chloroauric acid, potassium tetrachloroplatinate (II), sodium tetrachloropalladate (II), silver nitrate, and combinations thereof.

The reducing agent may be any agent capable of reducing the inorganic material cations to the elemental, zero-valence form. In some embodiments, the reducing agent comprises HEPES, ascorbic acid or a combination thereof. In one embodiment, the inorganic material comprises gold and the reducing agent comprises HEPES. In another embodiment, the inorganic material comprises platinum and the reducing agent comprises HEPES, ascorbic acid, or a combination thereof. In yet another embodiment, the inorganic material comprises palladium and the reducing agent comprises ascorbic acid. In still another embodiment, the peptoid includes at least one residue with a side chain derived from tyramine, and the peptoid functions as the reducing agent.

The method can be performed at any temperature suitable to form the hybrid organic/inorganic material from the peptoid and the inorganic material. In some embodiments, the temperature ranges from ambient temperature (e.g., 20-25° C.) to 70° C., such as from 20° C. to 60° C., 20° C. to 50° C., 20° C. to 40° C., or 20° C. to 35° C.

Peptoid sequence design may be based at least in part on a desired architecture of the hybrid organic/inorganic material and/or the composition of the inorganic material. For example, the specific arrangement of side chains may be designed and selected based on the following principles. For peptoids to induce dendritic or spherical dendritic architecture, the peptoid is designed to possess adequate hydrophobicity and strong binding affinity for the inorganic material. Decreasing hydrophobicity and/or binding affinity leads a trend toward spherical, non-dendritic particles.

In some embodiments, the inorganic material is gold, the desired architecture is dendritic or spherical dendritic, and the peptoid sequence includes at least some residues possessing amino-containing side chains and at least some hydrophobic residues. For example, the rings of Ndc residues have strong binding affinity for gold. Binding affinity is increased when the peptoid includes a terminal group of Ndc residues compared to peptoids having a group of Ndc residues in a mid-portion of the peptoid. Further inclusion of Nab and Nce residues (with amino- and carboxyl-containing side chains, respectively) in the peptoid provides amphiphilicity and inter-peptoid electrostatic interactions between Nce and Nab side-chain groups. A combination of amphiphilicity and strong peptoid-metal binding was found to provide a dendritic or spherical dendritic architecture. Peptoids including Ndc, Nce and Nab groups were found to provide a spherical dendritic, or coral-shaped, architecture when the inorganic material was gold. Because Nae has similar properties to Nab, peptoids including Nae in place of Nab also provide a coral-shaped architecture. Conversely, if peptoid-metal binding affinity and/or hydrophobicity are decreased, the resulting architecture trends toward spherical with little or no dendritic character. For example, when the peptoid includes Ndc residues in the mid-portion of the peptoid instead of terminal Ndc residues, the resulting architecture is spherical with little or no dendritic character.

The peptoid sequence also may be selected, in part, based upon the composition of the inorganic material. As discussed above, Ndc residues provide strong binding to gold. Ndc residues, particularly terminal Ndc residues, also provide strong binding to platinum and palladium. In contrast, the Nce residues with side chains derived from β-alanine provide strong binding to silver.

Figure 3:
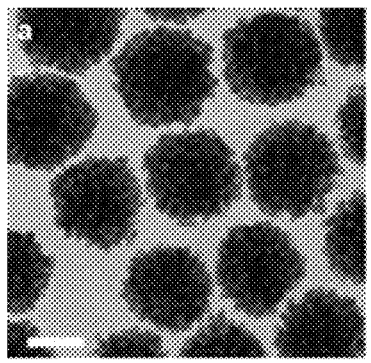
FIG. 3 is a transmission electron microscope (TEM) image of nanoparticles of a hybrid organic/inorganic nanomaterial comprising peptoid-1 (Pep-1) and gold; scale bar=50 nm.
Figure 42A:
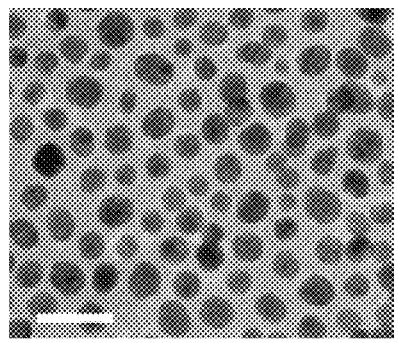
FIGS. 42A and 42B are TEM images showing nanoparticles of Pep-1/gold nanomaterial formed at pH 5.5; scale bars=20 nm (42A), 6 nm (42B).
Figure 42B:
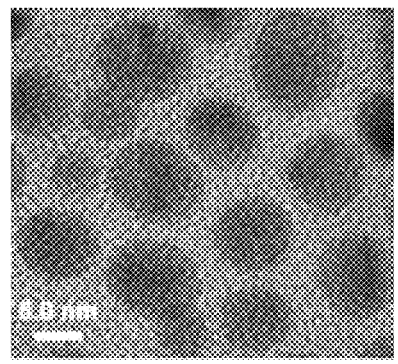

Architecture also may be influenced by pH. For instance, at lower pH (e.g., pH 5.5) where carboxyl groups are protonated, amphiphilicity and inter-peptoid interactions may be greatly reduced compared to reactions performed under neutral or mildly alkaline conditions. In one example, a reaction with Pep-1 and gold at pH 7.3 provided a spherical dendritic architecture (FIG. 3), whereas a reaction with Pep-1 and gold at pH 5.5 induced formation of nearly spherical particles with little or no dendritic character (FIGS. 42A, 42B).

Thus, when spherical dendritic particles are desired and the inorganic material comprises Au, Pt, Pd, or a combination thereof, the peptoid may include (i) a group of terminal Ndc residues to provide hydrophobicity and enhance binding affinity to the inorganic material and (ii) at least some Nab and Nce residues to provide amphiphilicity and inter-peptoid electrostatic interactions. In some embodiments, the peptoid may include a group of at least four terminal Ndc residues. The peptoid may include one or more groups of Nab residues and one or more groups of Nce residues, with each group including four or more residues, such as 4-12 residues. The reaction may be performed at neutral or mildly alkaline conditions such that carboxyl groups on the peptoid are deprotonated. In contrast, if a spherical, non-dendritic architecture is desired, the peptoid may include Ndc residues in its mid-portion and/or the pH may be reduced such that carboxyl groups are protonated.

In one application, described at a high level, peptoids (e.g., peptoids including Nce, Nab, and Ndc residues) were combined with gold nanoparticles produced by reduction of a gold salt or acid. The peptoid-stabilized gold nanoparticles were combined in a controlled spherical coral-shaped particle formation. During the early stages of particle formation the structure of the various components, particularly the existence and placement of the —NH$_2$ side chains and strongly hydrophobic Ndc groups in the chains induced the formation of distorted nanorods and the random attachment of peptoids to the nanorods by providing both peptoid gold binding affinity and peptoid hydrophobicity. This in turn enabled morphological control over the arrangement and placement of peptoids and the inorganic materials in the structure. The resulting stable coral-shaped particles exhibited sharp plasmon resonances at 528 nm with a plasmonic enhancement factor on the order of $10^5$. In another example, coral-shaped Pd- and Pt-containing nanomaterials were prepared.

Figure 52:
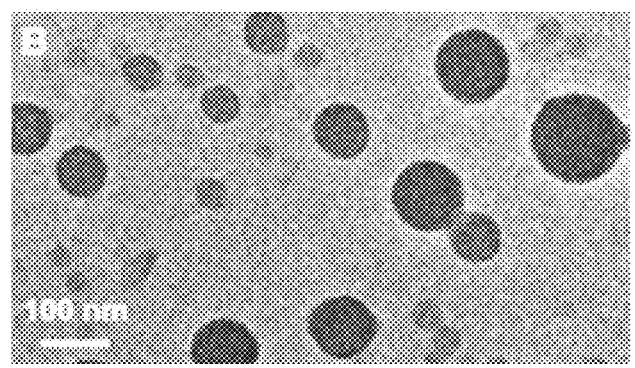
FIG. 52 is a TEM image showing nanoparticles of a Pep-11/polyhedral oligomeric silsesquioxane (POS) nanomaterial with a nanovesicle architecture; scale bar=100 nm.
Figure 53:
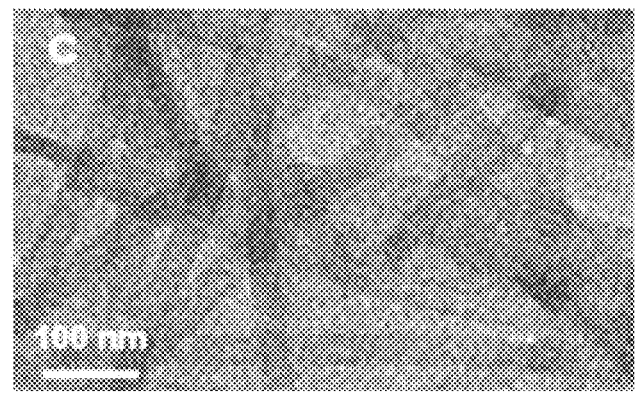
FIG. 53 is a TEM image showing highly ordered nanotubes formed when Pep-11 was combined with the Pep-11/POS nanomaterial of FIG. 52; scale bar=100 nm.

In certain embodiments, the hybrid material comprises POS as building blocks. Covalent attachment of POS to self-assembling peptoids provides hybrid materials having hierarchical structures and the precisely controlled stereochemistry of the POS building blocks. The incorporation of POS provides the resulting hybrid materials with good TEM contrast, suggesting that fluid-cell TEM may be used to monitor the assembly of POS-peptoid based hybrid materials in real time. In some instances, the POS may be sufficiently bulky to alter the desired architecture of peptoid assembly. For example, simply combining POS with self-assembling peptoids, such as tube-forming Pep-11, may result in a spherical or vesicle-like architecture (FIG. 52). However, a co-assembly of POS-Pep-11 with additional Pep-11 (e.g., at a 2:1 molar ratio of peptoid to POS-peptoid) instead produces ordered nanotubes (FIG. 53). Thus, in some embodiments, the method may include initially combining the peptoid and POS under conditions such that the peptoid and the POS form an initial hybrid organic/inorganic material having a first architecture, and subsequently combining the initial hybrid organic/inorganic material with additional peptoid under conditions such that the initial hybrid organic/inorganic material and additional peptoid form a subsequent hybrid organic/inorganic material having a second architecture different than the first architecture.

III. HYBRID ORGANIC/INORGANIC MATERIALS

Embodiments of the disclosed hybrid organic/inorganic materials comprise a plurality of peptoids and an inorganic material. The inorganic material may be solely inorganic or an inorganic-organic material (e.g., a silicon-organic material). Each peptoid comprises a specific arrangement of side chains on the residues. In some embodiments, the inorganic material comprises a metal, such as a metal in a zero valence state. In certain embodiments, the inorganic material comprises Au, Pd, Pt, Ag, TiO$_2$, iron oxide, a silica, or any combination thereof. In some examples, the inorganic material is Au, Pd, or Pt. In an independent embodiment, the hybrid material comprises a POS.

The hybrid organic/inorganic material comprises a plurality of nanoparticles comprising the inorganic material, wherein the nanoparticles are randomly attached to one another via the plurality of peptoids, thereby forming a cluster of nanoparticles joined by the peptoids. Attachment is provided by peptoid-peptoid and peptoid-nanoparticle surface interactions. The hybrid organic/inorganic material has an architecture, which is based at least in part on the peptoid sequence.

In some embodiments, the hybrid materials are comprised of nanorods as building blocks, wherein the nanorods are randomly attached together by peptoids via peptoid-surface interactions with the nanorods and peptoid-peptoid interactions (FIG. 2). Each nanorod may be formed by the merging, or joining, of a plurality of smaller nanoparticles, such as smaller, substantially spherical nanoparticles. The nanorods may be "distorted nanorods" (see, e.g., FIGS. 5, 7, 9A).

A portion of a peptoid may adsorb onto an outer surface of a nanoparticle, such as the outer surface of a nanorod. In some embodiments, as additional smaller nanoparticles deposit onto the larger nanoparticle, at least part of the adsorbed portion of the peptoid may become partially or completely embedded within the larger nanoparticle as it grows. Nanoparticles are randomly attached together when (i) a portion of a peptoid adsorbs to an outer surface of a first nanoparticle and another portion of the peptoid adsorbs to an outer surface of a second nanoparticle, or (ii) the peptoid interacts directly or indirectly with another peptoid that is adsorbed to the outer surface of a second nanoparticle.

Figures 22A, 22B:
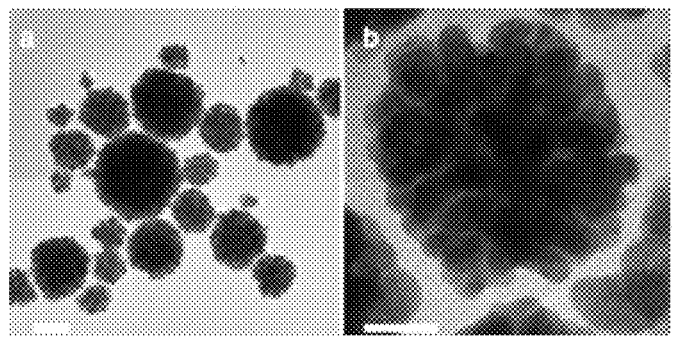
FIGS. 22A-22B are TEM images showing nanoparticles of Pep-4/gold nanomaterial; 22A scale bar=50 nm, 22B scale bar=20 nm.

The architecture of the hybrid organic/inorganic material is based at least in part on the peptoid sequence, i.e., the specific arrangement of side chains. In some embodiments, the architecture is spherical, dendritic, or spherical dendritic. A spherical architecture means that particles of the material appear generally spherical when viewed under magnification, e.g., with a TEM (see, e.g., FIG. 37). Spherical does not mean that the particles appear as perfectly smooth spheres. A dendritic architecture means that the particle appears to have a plurality of branches, e.g., a "coral" shape (see, e.g., the cluster of distorted nanorods in FIG. 2). A spherical dendritic architecture refers to a dendritic architecture with branches generally extending outward from a core of the particle thereby giving the dendritic particle a generally spherical shape, e.g., a spherical coral shape (see, e.g., FIGS. 3, 5, 22B).

In an independent embodiment, the inorganic material is a POS and the hybrid organic/inorganic nanoparticles are substantially spherical (see, e.g., FIG. 52). Reaction of the spherical hybrid nanoparticles with additional peptoids provides a subsequent hybrid organic/inorganic nanomaterial comprising ordered nanotubes (see, e.g., FIG. 53).

Exemplary non-limiting examples of the hybrid organic/inorganic materials disclosed herein include Pep-1/Au, Pep-2/Au, Pep-3/Au, Pep-4/Au, Pep-7/Au, and Pep-8/Au with a spherical dendritic architecture; Pep-9/Au and Pep-10/Au with a spherical (non-dendritic) architecture; Pep-1/Pt and Pep-1/Pd with a spherical dendritic architecture; and Pep-11/POS with an ordered nanotube architecture.

In some embodiments, the hybrid inorganic/organic materials are very stable and remain intact with the architecture remaining unchanged. For example, the architecture may be retained at elevated temperatures, in salt-containing solutions, or when stored for extended periods of time, e.g., for several days, weeks, or months. In one example, particle architecture was retained after incubation in water at 60° C. for 30 hours. In another example, particle architecture was retained after storage in 1.0 M aqueous NaCl for 5 days.

Advantageously, at least some embodiments of the disclosed hybrid organic/inorganic nanomaterials having a dendritic or spherical dendritic architecture exhibit enhanced plasmonic resonance compared to nanoparticles of the inorganic material alone or hybrid organic/inorganic nanomaterials having a spherical, non-dendritic architecture. For example, when the architecture is dendritic or spherical dendritic, gold particles of the hybrid organic/inorganic nanomaterials may exhibit a sharp plasmon resonance (e.g., at 528 nm in some embodiments) and/or have a high plasmonic enhancement on the order of up to $10^5$, such as from 10 to $10^5$.

IV. USES

Potential applications for this methodology and its related products include biological imaging and sensors, e.g., sensors for detecting pesticides agricultural applications (see, e.g., Stewart et al., *Chem Rev* 2008, 108:494-521). For imaging applications, the hybrid organic/inorganic materials may be administered to a subject by any suitable means and subsequently visualized by conventional diagnostic imaging methodologies. In some embodiments, particles of the hybrid organic/inorganic materials may be conjugated to a targeting molecule (e.g., an antibody or ligand) as will be understood by one of ordinary skill in the art of diagnostic imaging, whereby the conjugate is capable of binding to a target, e.g., a target within a subject, such as a human or non-human mammal, and allowing the target to be visualized. Embodiments of the disclosed method also can be used for biomimetic synthesis of functional materials and for understanding biocontrolled crystallization. For materials infrastructure, embodiments of the disclosed peptoid-based method could be used for synthesizing functional hybrid materials on demand for solar cell and battery applications, catalysis and other applications.

V. REPRESENTATIVE EMBODIMENTS

Certain representative, non-limiting embodiments of the disclosed method and compositions are shown in the following numbered paragraphs.

1. A method for producing hybrid organic/inorganic materials having a preselected structure comprising the steps of: exposing a preselected peptoid to a preselected inorganic material under preselected conditions whereby assembly of the peptoid and the inorganic material takes place to form the hybrid organic/inorganic structure having the preselected structure.

2. The method of paragraph 1 wherein the preselected structure is an ordered 3D structure.

3. The method of paragraph 2 wherein the preselected structure is spherical.

4. The method of paragraph 2 wherein the preselected structure is coral-shaped.

5. The method of paragraph 1 wherein the preselected peptoid includes a side chain with a desired hydrophobic activity.

6. The method of paragraph 5 wherein the preselected peptoid includes at least one amino- (—NH$_2$) containing side chain.

7. The method of paragraph 6 wherein the preselected peptoid side chain includes a specific arrangement of Nce, Ndc, and Nab groups.

8. The method of paragraph 5 wherein the preselected inorganic material is gold (Au(111)).

9. The method of paragraph 7 wherein the preselected peptoid includes (Pep-1-Pep-3, in which Nce=N-(2-carboxyethl)glycine, Nab=N-(4-aminobutyl)glycine, and Ndc=N-[2-(2,4-dichlorophenyl)ethyl]glycines.

10. The method of paragraph 1 wherein the preselected structure includes a random attachment of distorted nanorods.

11. The method of paragraph 1 wherein the preselected inorganic component is located within a polyhedral oligomeric silsesquioxanes (POS) nanocluster.

12. The method of paragraph 11 wherein the preselected peptoid is Pep-4.

13. The method of paragraph 11 wherein the preselected structure is an ordered nanotube.

14. A hybrid organic/inorganic material comprising a plurality of organic peptoids functionally connected to an inorganic material in a preselected arrangement.

VI. EXAMPLES

General Methods and Materials

Materials. All solvents and chemicals were of analytical grade and were obtained from commercial sources and used without further purification. 0.2M HEPES buffer (4-(2-hydroxyethyl)-1-piperazineethanesulfonic acid) was made by directly diluting 1.0 M HEPES buffer (pH=7.3±0.1; Fisher Scientific) with ultrapure water. The ultrapure water was obtained from a Milli-Q water purification system (Millipore Corp., Bedford, Mass.) with resistivity of 18.2 MΩ·cm.

Transmission electron microscopy (TEM) characterization. TEM images were taken on the FEI Tecnai G2 transmission electron microscope and JEM 2100 (JEOL) with an accelerating voltage of 200 kV. The samples were prepared by pipetting one drop of solution onto a 3-mm-diameter copper grid coated with carbon film.

Liquid phase TEM (LP-TEM). LP-TEM was done by using a standard Hummingbird static cell on a Hummingbird Scientific's Liquid flow holder. The liquid layer for the in situ TEM experiment was formed in the fluid stage tip by sealing two silicon chips (Hummingbird Scientific, USA), with a 50×200 µm$^2$ opening etched from the center, which had a 50 nm thick amorphous SiN membrane to form the electron transparent window for observation. The two chips are separated by a 100 nm spacer that allows the passage of incident electrons. The silicon chips were treated for 40 seconds with plasma (Harrick Plasma) cleaning to make them totally hydrophilic before assembling liquid cell. The bottom chip was firstly placed with membrane side up inside the well-cleaned fluid stage tip, and a 0.6 µL stock solution was placed onto its central spot with a pipette. The top chip was then placed membrane side down to align well with the bottom chip, and a transparent window can be observed under a stereo microscope. Finally the liquid cell holder was placed in a pump station (Pfeiffer vacuum) to test the vacuum condition before loading it to the microscope, which was kept for at least 5 minutes when the vacuum reached very well. Bright field images were recorded with an Eagle CCD detector, which was made into a movie using the movie maker software.

Time-of-flight secondary ion mass spectrometry (ToF-SIMS). ToF-SIMS measurements were acquired using a ToF.SIMS5 instrument (IONTOF GmbH, Monster, Germany) (located at PNNL, Richland, Wash.). For peptoid adsorption studies, freshly-cleaned Au(111) substrates (100 nm Au deposited on silicon substrates with 20 nm Cr as an adhesion layer) were incubated in corresponding peptoid aqueous solutions (pH=7.3) for overnight, then washed thoroughly with water and dried by $N_2$ blowing for ToF-SIMS studies.

X-ray photoelectron spectroscopy (XPS). The peptoid-Au (111) samples used for XPS measurements were prepared using a same method that was described above to prepare TOF-SIMS samples: freshly-cleaned Au(111) substrates were incubated with corresponding peptoids aqueous solutions (pH7.3 or pH5.5) for overnight, they were then washed thoroughly with water and dried by $N_2$ blowing for XPS studies. XPS data were acquired using a Physical Electronics Quantera Scanning X-ray Microprobe. This system uses a focused monochromatic Al Kα X-ray (1486.7 eV) source for excitation and a spherical section analyzer. The instrument has a 32 element multichannel detection system. The X-ray beam is incident normal to the sample and the photoelectron detector is at 45° off-normal. High energy resolution spectra were collected using a pass-energy of 69.0 eV with a step size of 0.125 eV. For the Ag $3d_{5/2}$ line, these conditions produced a FWHM of 0.92 eV±0.05 eV. The binding energy (BE) scale is calibrated using ISO 15472 Ed. 2 Surface Chemical Analysis—XPS—Calibration of energy scales. The Cu $2p_{3/2}$ feature is set at 932.62±0.05 eV and Au $4f_{7/2}$ line is set at 83.96±0.05 eV. Quantification was performed using Ulvac-phi Inc., MultiPak software version 9.1.1.7.

Three-photon photoemission electron microscopy (TP-PEEM). Photoemission from the spherical coral-shaped gold nanoparticles was imaged using a photoemission electron microscope (Elmitec, PEEM III). The sample is mounted approximately 2 mm from an electrically grounded objective lens. A −20 kV electronic potential is applied to the sample in order to accelerate and transfer the photoelectrons to an imaging column containing a series of electro-magnetic lenses which focus and project the photoelectron image onto a microchannel plate/phosphor screen detector. Images are acquired with a computer controlled charge-coupled device camera. The base pressure of the microscope chamber is ~9×10$^{-11}$ Torr, and increases to ~5×10$^{-10}$ Torr throughout the measurements. The sample was irradiated with laser pulses centered at 780 nm, from a 90 MHz Titanium-Sapphire femtosecond oscillator (Griffin-10, KM Labs). Following external prism pair compression transform limited pulses, of 15 fs duration, were delivered to the sample chamber. The laser is focused to a ~8×10$^{-3}$ mm$^2$ area, and its polarization is controlled using a half wave plate.

Hyperspectral UV-Vis extinction microscopy and TP-PEEM studies. Hyperspectral UV-Vis extinction microscopy experiments measurements were achieved by coupling a hyperspectral detector (Surface Optics Corp.) to a conventional confocal optical microscope. In this study, the incident broad band depolarized light source was transmitted through the sample, consisting of a sparse distribution of spherical coral-shaped gold nanoparticles on a glass coverslip, using a bright field condenser. Hyperspectral extinction images are represented as −log($I_{sample}/I_{substrate}$), in which $I_{sample}$ is the spatially (130 nm$^2$/pixel) and spectrally (375-800 nm, Δλ=4.7 nm) resolved intensity across the sample, and $I_{substrate}$ is the reference hyperspectral intensity image collected from the blank underlying glass coverslip.

In typical ensemble-averaged colloidal UV-Vis measurements, several factors come into play in the interpretation of the recorded optical signals. Those include but are not limited to (i) the solvent/medium of choice (Jensen et al., *J Phys Chem B* 1999, 103:9846-9853), (ii) the possibility of inter-particle aggregation/coupling in solution (Whitmore et al., *J Phys Chem C* 2011, 115:15900-15907), and (iii) size and structural heterogeneity (Peppernick et al., *J Chem Phys* 2013, 138(15):154701). Whereas (i) affects the recorded response in an understandable manner, both (ii) and (iii) may obfuscate the interpretation of the recorded optical spectra. In contrast, the individual particle measurements described herein exclusively report on the plasmonic response of the synthesized coral-shaped particles. However, there are limitations to this optical measurement; it is diffraction-limited, and in its present form, does not offer a direct measurement of the plasmonic enhancement factor supported by spherical coral-shaped particles. To this end, TP-PEEM measurements were also performed. The PEEM setup has been previously described elsewhere in great detail (Gong et al., *Nano Lett* 2015, 15:3472-3478; Gong et al., *J Phys Chem Lett* 2014, 5:4243-4249). The two aspects of multiphoton PEEM of particular interest to this report are its ability (i) to image the plasmonic fields of the synthesized plasmonic coral-shaped particles, and (ii) to provide an estimate of the enhancement factor supported by these superstructures (Peppernick, et al., *J Chem Phys* 2013, 138(15); 154701; Peppernick et al., *J Chem Phys* 2011, 134(3):034507).

Molecular Dynamics Simulations

To predict the conformational ensemble of the surface-adsorbed peptoids, REST-MD simulations comprising a single chain of each of three peptoids, Pep-1 (with two different protonation states, corresponding with pH 5.5 and pH 7.3), Pep-5, Pep-6 and Pep-7, adsorbed at the aqueous Au(111) interface were performed. To probe inter-chain interaction effects, standard MD simulations of a two-chain surface-adsorbed peptoid system were also carried out. Finally, to estimate and compare the adsorption free energy of dichlorobenzene and benzene were performed, multiple walker well-tempered metadynamics simulations, comprising a single adsorbate (dichlorobenzene and benzene) and the aqueous Au(111) interface. Simulation details are provided below.

General Simulation Set-up Details: An orthorhombic periodic cell was used, and periodic boundary conditions were applied in all three dimensions. All simulations were performed in the Canonical (NVT) ensemble, at a temperature of 300K, maintained using the Nosé-Hoover thermostat (Nose, *Mol Phys* 1984, 52:255-268; Hoover, *Phys Rev A* 1985; 31:1695-1697), with a coupling constant of $\tau$=0.2 ps. Newton's equations of motion were solved using the leap-frog algorithm with an integration time-step of 1 fs. Coordinates and velocities were saved every 1000 steps (1 ps). Long-ranged electrostatic interactions were treated using Particle-mesh Ewald (PME) (Darden et al. *J Chem Phys* 1992, 98:10089-10092), with a cut-off at 11 Å, whereas a force-switched cut-off, starting at 9 Å and ending at 10 Å was used for Lennard-Jones non-bonded interactions.

The GoIP-CHARMM(12) force-field was used to model the Au slab. The peptoids were described based on the force-field published by Jin and co-workers (*Nat Commun* 2016, 12252), and water was described using the SPC/E (Berendsen et al., *J Phys Chem* 1987, 91:6269-6271) model. Where needed, counter-ions ($Na^+$ atoms) were added to ensure overall charge-neutrality of the cell, with the Dang95 interaction parameters (Dang et al., *JACS* 1995, 117:6954-6960). All metal atoms in the slab were held fixed in space during these simulations, with only the metal atom dipoles able to freely rotate. Random initial dipole positions were used throughout. Recent tests indicate that there is very little difference between binding obtained using a rigid substrate, vs. using a slab where all atoms can move (Wright et al., *Mol Simul* 2013, 39:1093-1102).

Replica Exchange with Solute Tempering Molecular Dynamics (REST-MD) Simulations: The system comprised one peptoid chain (one of Pep-1, Pep-5, Pep-6 or Pep-9); a Au slab, five atomic layers thick, presenting the (111) surface on both slab faces; and, ~11,000 SPC water molecules. The dimensions of the simulation cell were ~59× 61×68 Å. The dimension of the periodic cell perpendicular to the slab plane was adjusted such that the density of liquid water in the center of the space between the slab and its periodic image recovered the target density of bulk liquid water at 300 K using the SPC model.

The implementation of REST exploits the replica exchange and free energy perturbation theory functionalities within Gromacs 5.0.1 (Hess et al., *J Chem Theory Comput* 2008, 4:435-447). Details of the Terakawa implementation (Terakawa et al., *J Comput Chem* 2011, 32:1228-1234) of REST have been provided previously (Palafox-Hernandez et al., *Chem Mater* 2014, 26:4960-4969). In the REST simulations, an 'effective temperature' window of 300-430K was spanned with 16 replicas. The initial configurations for each replica covered a range of conformations. The adsorbate structure for each replica was initially placed such that at least one peptoid atom was found within ~3A distance from the top surface of the Au slab. The 16 values of lambda used to scale the force-field were:

$\lambda_j$=0.0000, 0.057, 0.114, 0.177, 0.240, 0.310, 0.382, 0.458, 0.528, 0.597, 0.692, 0.750, 0.803, 0.855, 0.930, 1.0000.

Prior to each REST simulation, initial configurations of each of the 16 replicas were equilibrated at their target potential for 0.5 ns, with no exchange moves attempted during this time. During the REST simulations, the interval between exchange attempts was set to 1000 MD steps (every 1 ps). All production REST simulations were run for a total of $20 \times 10^6$ MD steps (20 ns). Frames from the trajectory were saved every 1 ps.

REST MD clustering analysis: Detailed analysis was carried out on the constant-ensemble run at an effective temperature of 300K (herein referred to as the reference trajectory). The Boltzmann-weighted ensemble was classified from reference trajectories into groups of like structures, on the basis of similarity of their backbone structures, via the Daura clustering algorithm (Daura et al., *Angew Chem Int Ed* 1999, 38:236-240) with a root mean-squared deviation (RMSD) cutoff between the positions all peptoid backbone atoms. A cutoff of 2.5 Å was used; the inventors' extensive experience based on clustering analyses of peptides of different lengths guided the identification of this cutoff value to be reasonable in this instance. The clustering analysis was performed over the entire 20 ns trajectory in each case. The population of a given cluster was calculated as the percentage fraction of the number of frames that were assigned membership of that cluster, divided by the total number of frames in the trajectory. The cluster with the largest population corresponds with the most likely structure of the peptoid in the interface-adsorbed state.

REST MD Contact Residue analysis: To quantify residue-surface contact, first, for each reference trajectory, the distance between the topmost layer of the Au surface and each residue in the peptoid sequence. On the basis of these data, distance cut-offs were established to identify a range of separations where each particular residue was in immediate contact with the Au surface was calculated. The fraction of frames in the reference trajectory for which each residue was found within the contact range of surface-residue separation was then calculated. A residue was then defined to be a contact residue if that residue was found to bind persistently to the surface. The residue-surface distance was defined based on the vertical separation between an assigned site on each residue side-chain, and the top/bottom layer of the Au slab. These residue side-chain sites comprised the carbon atom of the carboxylate group, the nitrogen atom of the ammonium group, and the center of the aromatic ring for the Nce, Nab, and Nxpe/Ndc respectively. The cut-off distances for each residue type were set to 5.5 Å for Nce and Nab, 4.0 Å for Nxpe (X=H) and 4.5 Å for Ndc.

Metadynamics Simulations: The system comprised: one adsorbate (either benzene or di-chlorobenzene); a Au slab, five atomic layers thick, presenting the (111) surface on both slab faces; and, 2040 SPC water molecules. The dimensions of the simulation cell were ~59×61×68 Å. The dimension of the periodic cell perpendicular to the slab plane was adjusted such that the density of liquid water in the center of the space between the slab and its periodic image recovered the target density of bulk liquid water at 300 K using the SPC model.

The free energy of adsorption of both benzene and di-chlorobenzene at the aqueous Au(111) interface was calculated using GROMACS (Hess et al., *J Chem Theory Comput* 2008, 4:435-447) in partnership with the PLUMED 2.2 software package (Tribello et al., *Comput Phys Commun* 2014, 185:604-613). Four different starting configurations of the adsorbate were used to perform Multiple Walkers Metadynamics simulations (Raiteri et al., *H Phys Chem B* 2006, 110:3533-3539), for the purpose of improving configurational sampling. A bias was applied to the centre of mass (c.o.m.) of the adsorbate in the direction perpendicular to the Au(111) surface, where the distance from the c.o.m. of the adsorbate ring to the Au(111) surface was defined as the collective variable (CV). These four initial configurations were used such that four different Gaussian potentials were added along the trajectory of the CV simultaneously at each time interval. Gaussians of 1.0 Å width were deposited every 1 ps, and the initial Gaussian height was set to 0.10 kJ mol$^{-1}$, while a bias factor of 10 was used.

The metadynamics simulations were run for 100 ns, in the canonical (NVT) ensemble at 300 K. The simulations were run until the fluctuations of the average free energy of adsorption had ceased changing appreciably as a function of time. The resulting free energy of adsorption was extracted using the integration method described in previous studies (Hughes et al., *J Mater Chem B* 2015, 3:3211-3221).

Example 1

Peptoid Synthesis

All peptoids were synthesized on a commercial AAPPTec Apex 396 robotic synthesizer (AAPPTec, Louisville, Ky.) on using a solid-phase submonomer cycle as described previously (Zuckerman et al., *J Am Chem Soc* 1992, 114: 10646-10647; Jin et al., *Nat Commun* 2016, 12252). All amine submonomers and other reagents used for peptoid synthesis were obtained from commercial sources and used without further purification. Rink amide resin (0.52 mmol/g, AAPPTec) was used to generate C-terminal amide peptoids. In this method, the Fmoc group on the resin was deprotected by adding 2 mL of 20% (v/v) 4-methylpiperidine/N,N-dimethylformamide (DMF), agitating for 20 min, draining, and washing with DMF. All DMF washes consisted of the addition of 1.5 mL of DMF, followed by agitation for 1 min (repeated five times). An acylation reaction was then performed on the amino resin by the addition of 1.6 mL of 0.6 M bromoacetic acid in DMF, followed by 0.35 mL of 50% (v/v) N,N-diisopropylcarbodiimide (DIC)/DMF. The mixture was agitated for 30 min at room temperature, drained, and washed with DMF. Nucleophilic displacement of the bromide with various primary amines occurred by a 1.6 mL addition of the primary amine monomer as a 0.6 M solution in N-methyl-2-pyrrolidone (NMP), followed by agitation for 60 min at room temperature. The monomer solution was drained from the resin, and the resin was washed with DMF as described above. The acylation and displacement steps were repeated until a polypeptoid of the desired length was synthesized. All reactions were performed at room temperature. Peptoid chains were cleaved from the resin by addition of 2.0 mL 95% (v/v) trifluoroacetic acid (TFA) in water for 35 min, which was then evaporated off under a stream of nitrogen gas. Following cleavage, peptoids were dissolved in 4.0 mL mixture (v/v=1:1) of water and acetonitrile for further purification.

All peptoids were purified by reverse-phase HPLC on an XBridge™ Prep C18 10 am OBD™ (10 μm, 19 mm×100 mm) column (Waters, Zellik, Belgium), using a gradient of 5-95% acetonitrile in $H_2O$ with 0.5% TFA over 15 min. The final products were analyzed using Waters ACQUITY reverse-phase UPLC (5-95% $CH_3CN$ in $H_2O$ at 0.4 mL/min over 5 min at 40° C. with a ACQUITY©BEH C18, 1.7 μm, 2.1 mm×50 mm column) that was connected with a Waters SQD2 mass spectrometry system. The final peptoid products were lyophilized at least twice from their solution in mixture (v/v=1:1) of water and acetonitrile. All lyophilized peptoids were finally divided into small portions (3.0×10$^{-6}$ mol) and stored at −80° C.

Structures of the synthesized peptoids and molecular weight of each peptoid as determined by mass spectrometry are shown below. The following monomer abbreviations were used to name the glycine residues:

Nce: N-(2-carboxyethyl)glycine; Ndc: N-[2-(2, 4-dichloro phenethyl)]glycine;

Nmc: N-[2-(4-chlorophenethyl)]glycine; Npe: N-[2-(X-phenethyl)]glycine;

Nab: N-(4-aminobutyl)glycine; Nae: N-(4-aminoethyl) glycine.

Peptoid-1 [(Nce)$_8$(Nab)$_4$(Ndc)$_4$]: 2483.0 (Molecular weight), 1242.8 (Found:[M/2+H]$^+$).

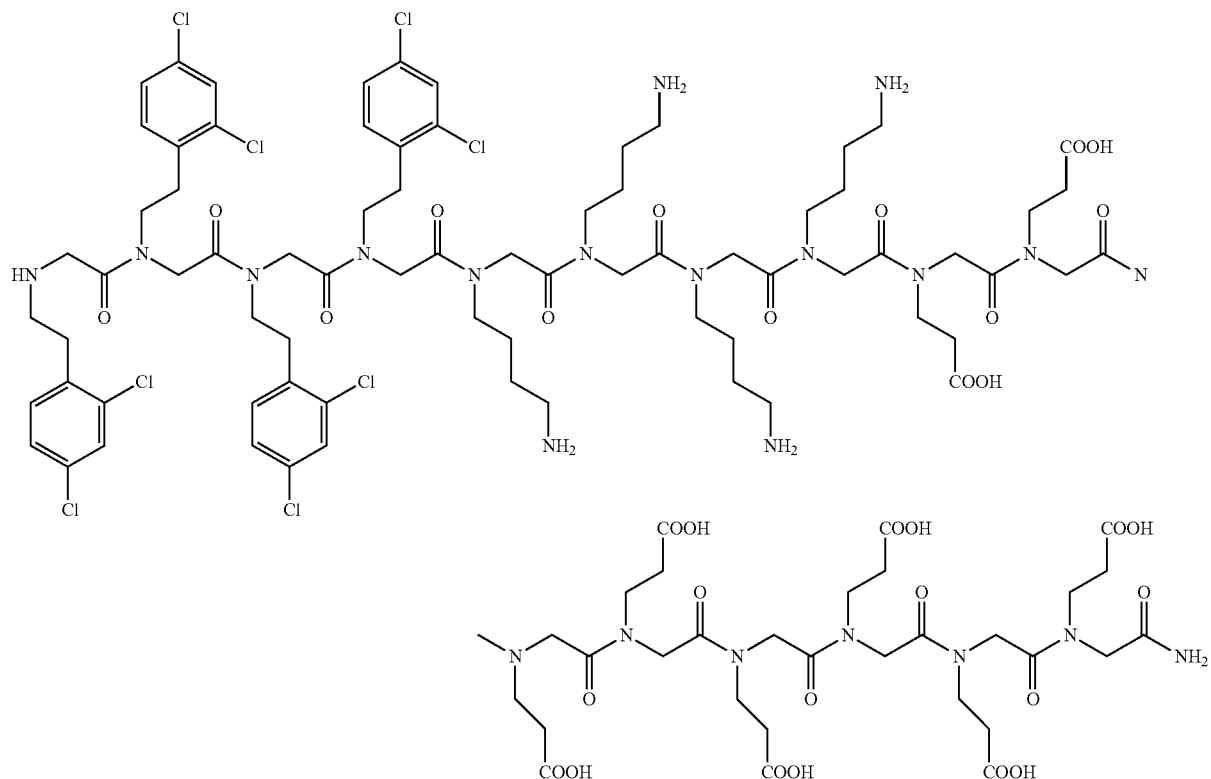
Peptoid-2 [(Nce)₁₂(Nab)₄(Ndc)₄]: 2999.5 (Molecular weight), 1500.4 (Found:[M/2+H]⁺).
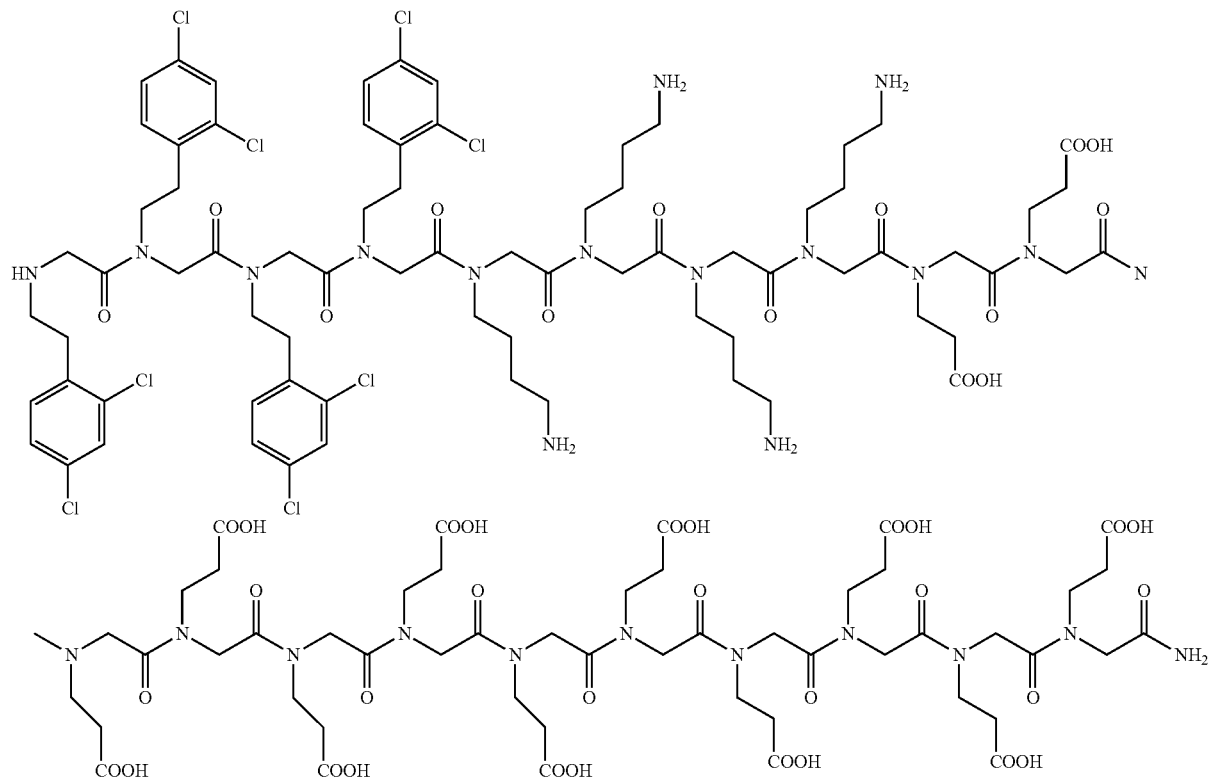

Peptoid-3 [(Nce)₄(Nab)₄(Ndc)₄]: 1966.5 (Molecular weight), 993.8 (Found:[M/2+H]⁺)
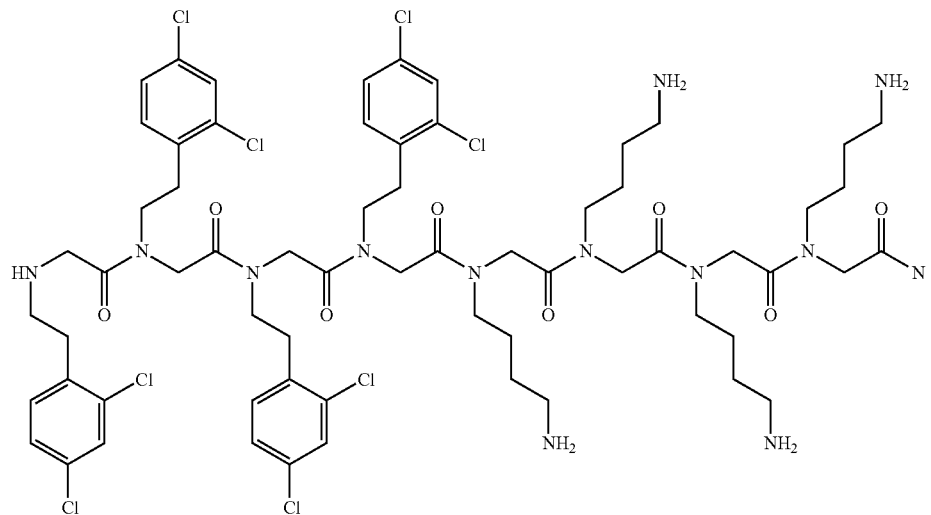
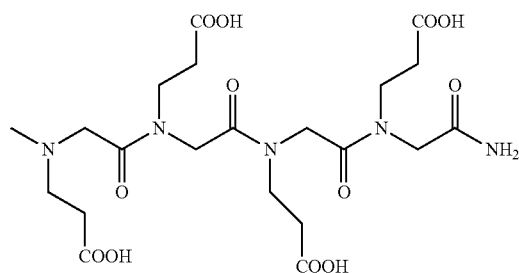
Peptoid-4 [(Nce)₈(Nab)₄(Nmc)₄]: 2341.9 (Molecular weight), 1172.8 (Found:[M/2+H]⁺).
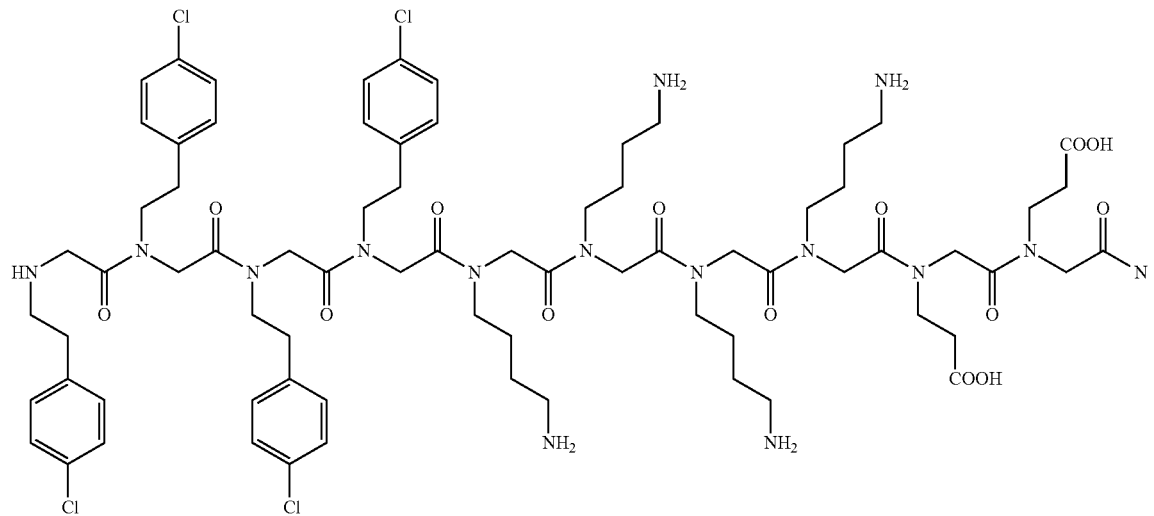

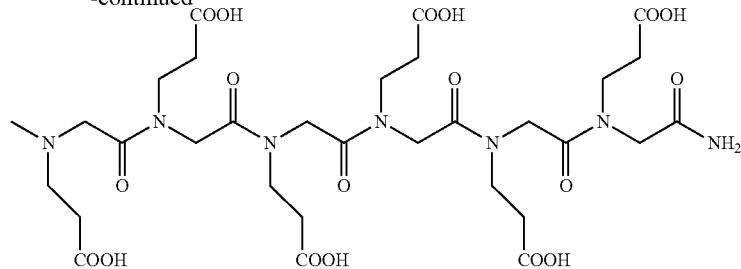
Peptoid-5 [(Nce)₈(Nab)₄(Npe)₄]: 2207.5 (Molecular weight), 1104.4 (Found:[M/2+H]⁺).
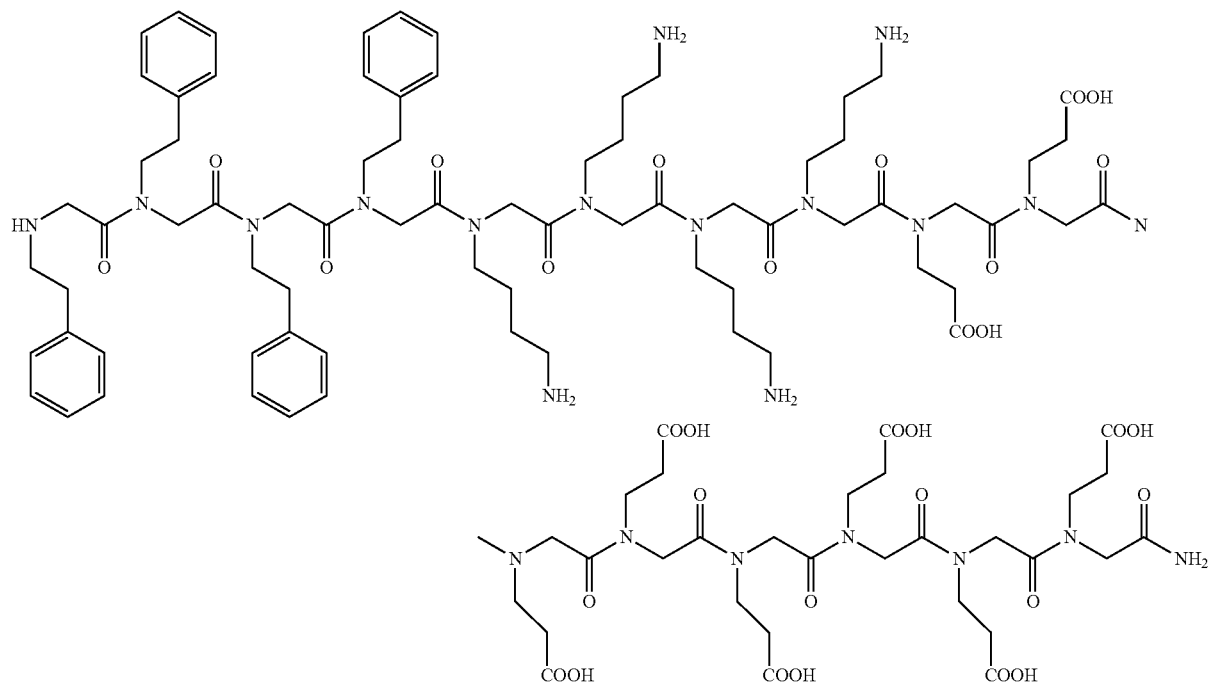
Peptoid-6 [(Nce)₈(Ndc)₄]: 1970.3 (Molecular weight), 1970.1 (Found:[M]).
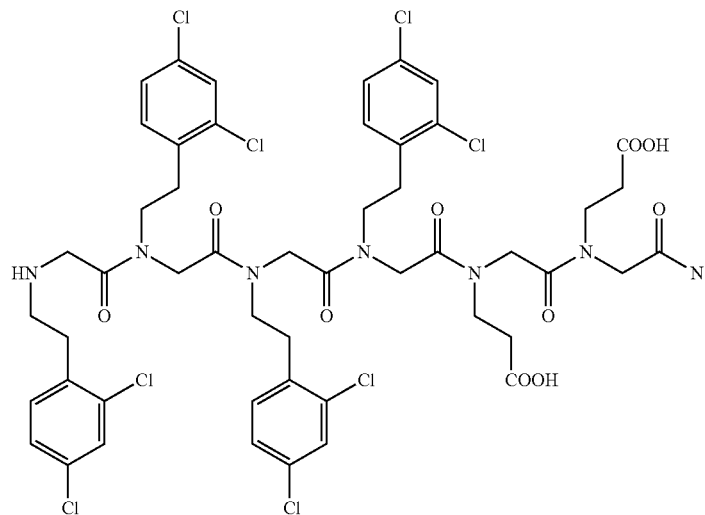

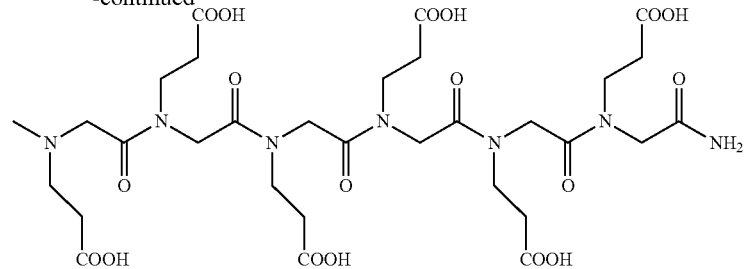
Peptoid-7 [(Nce)$_8$(Nae)$_4$(Ndc)$_4$]: 2370.8 (Molecular weight), 1186.1 (Found:[M/2+H]$^+$).
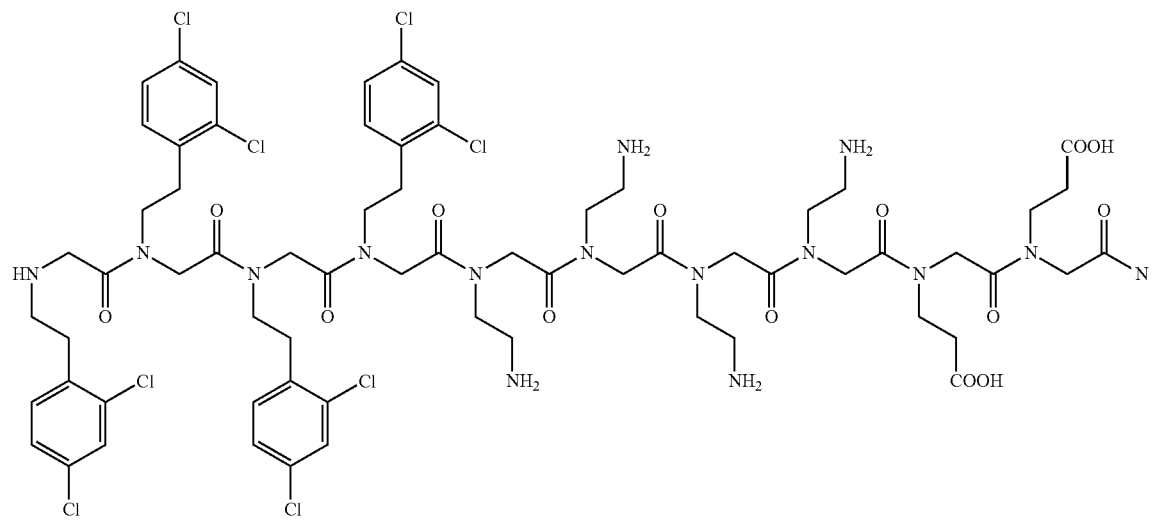
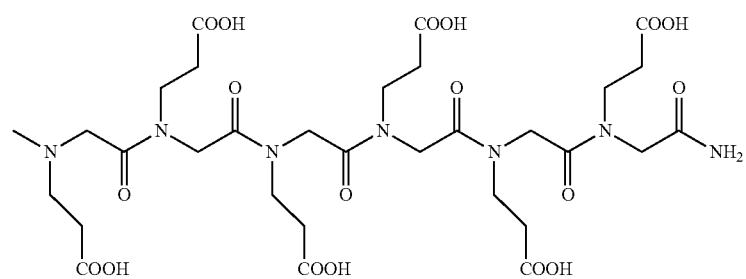

Peptoid-8 [(Nce)$_8$(Nab)$_1$(Ndc)$_4$]: 2098.48 (Molecular weight), 1050.05 (Found:[M/2+H]$^+$).
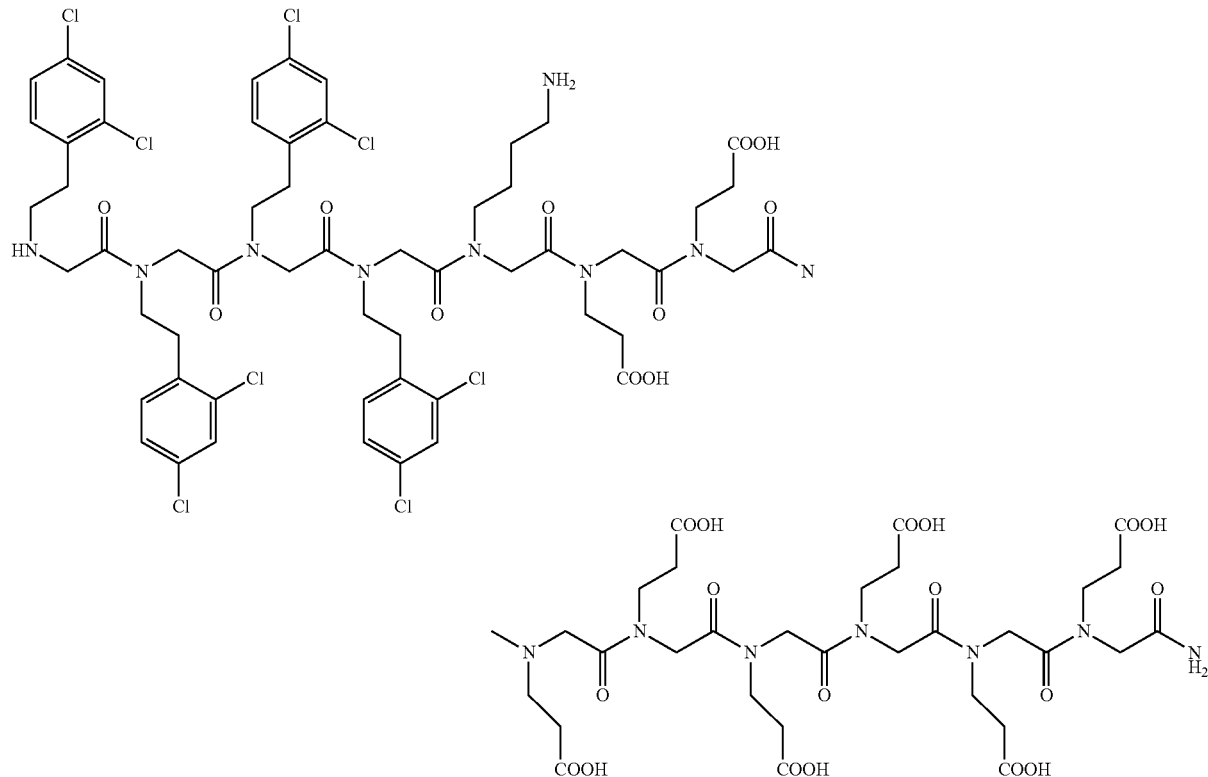
Peptoid-9 [(Nce)(Ndc(Nab)]: 1966.5 (Molecular weight), 983.2 (Found:[M/2+H]+
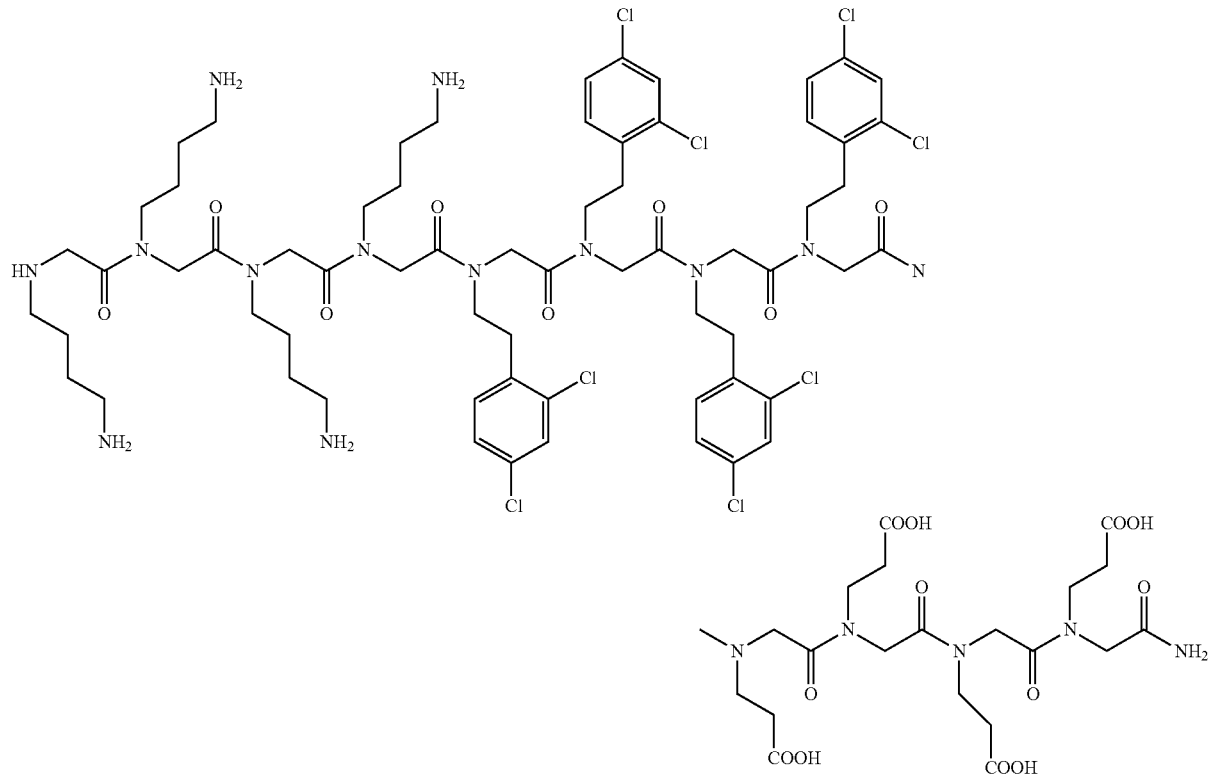

Peptoid-10 [(Nce)$_{12}$(Ndc)$_4$(Nab)$_4$]: 2999.5 (Molecular weight), 1000.5 (Found:[M/3+H]$^+$), 1501.3 (Found:[M/2+H]$^+$).

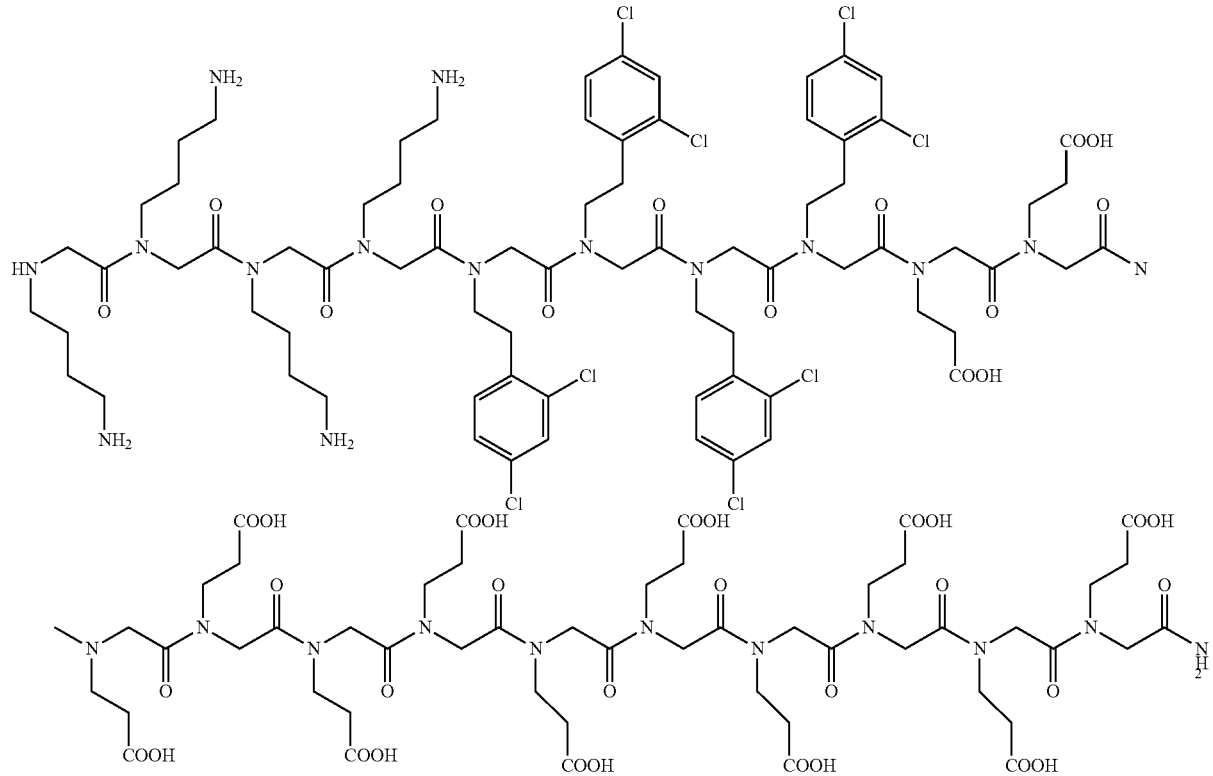

Example 2

Preparation and Characterization of Au-Based Nanomaterials

Lyophilized peptoids (3.0×10$^{-6}$ mol) were mixed with 1.5 mL ultrapure water in glass vial, and 10 μL saturated (NH$_4$)$_2$CO$_3$ solutions were used to facilitate dissolution. The final concentration of peptoid stock solution was 2.0 mM.

75 μL of 2 mM peptoid stock solution and 250 μL of 0.2 M HEPES buffer (pH=7.3±0.1; HEPES=4-(2-hydroxyethyl)-1-piperazineethanesulfonic acid) were added into 175 μL of water. HEPES is a weak capping and mild reducing agent. After 20 minutes, 6.0 μL of HAuCl$_4$ (0.1 M) was added and vortexed for 15 s to initiate nanoparticle formation. The solution was left undisturbed at room temperature. The resulting gold nanomaterials were formed after 5 h incubation.

Figure 4:
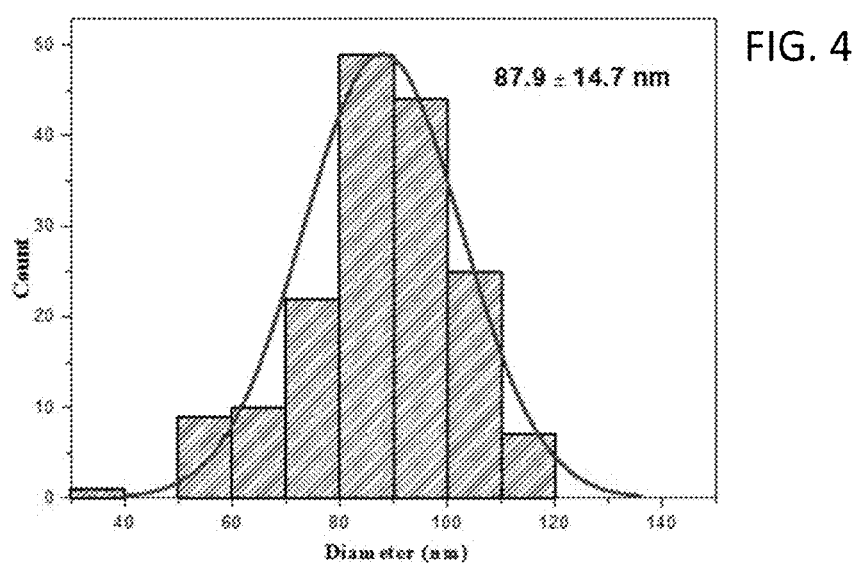
FIG. 4 is a graph showing the size distribution of the nanoparticles of FIG. 3.
Figure 6:
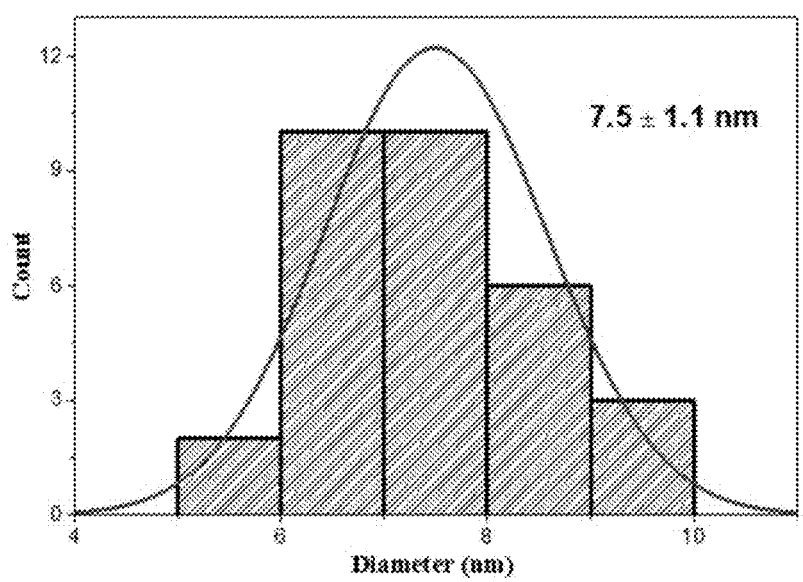
FIG. 6 is a graph showing the size distribution of nanorods within the nanoparticles of the Pep-1/gold nanomaterial.
Figure 8:
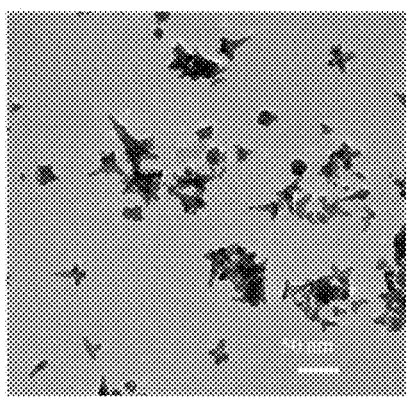
FIG. 8 is a TEM image showing formation of irregular gold nanoparticles formed in the absence of a peptoid; scale bar=50 nm.

TEM data showed that Pep-1 induced the formation of monodisperse spherical coral-shaped nanoparticles (FIG. 3) with an average particle diameter of 87.9±14.7 nm (FIG. 4). The nanoparticles were composed of distorted nanorods (FIG. 5) with an average diameter of 7.5±1.1 nm (FIG. 6). High-resolution TEM (HR-TEM) studies further confirmed this structure (FIG. 7) and revealed the distinct contrast between its core and peripheral branches. In the absence of Pep-1, the same reaction conditions led to the formation of irregular NPs (FIG. 8), demonstrating the significance of Pep-1 in the hedgehog particle formation.

Figure 9B:
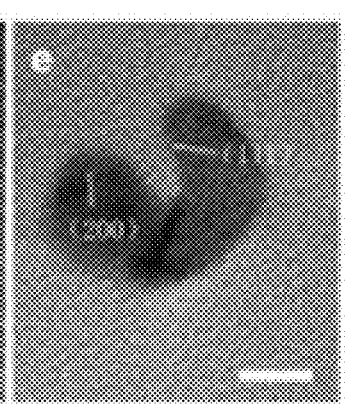
Figure 9C:
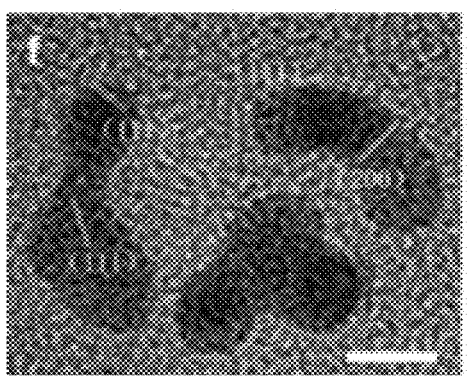
Figure 9D:
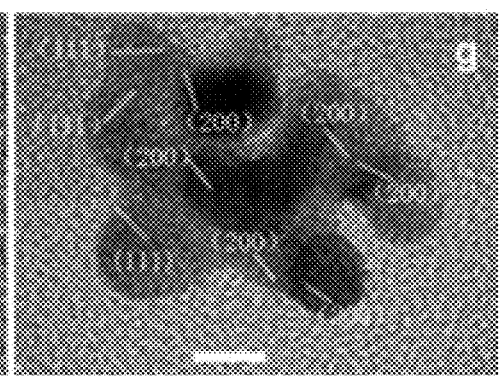

TEM results of early stages of spherical coral-shaped particle formation showed that Pep-1 induced formation of distorted gold nanorods with (111) lattice fringes (FIG. 9A) and clusters of nanorods with both (111) and (200) lattice fringes (FIGS. 9B-8D9), indicating that distorted nanorods were randomly attached together (non-oriented attachment) to form clusters. This formation pathway was further suggested by no observation of Pep-1 assemblies (FIG. 10) in the early stage of Pep-1-induced coral-shaped nanoparticle formation, and by the formation of similar coral-shaped particles (average diameter=37.4 nm±6.8 nm) at 60° C. (FIGS. 11, 12) or under continuously stirring conditions (FIG. 13). These coral-shaped particles are highly stable and remained intact after being exposed to 60° C. in water for 30 h (FIG. 14) or in 1.0 M aqueous NaCl solution for 5 days (FIG. 15).

To know more about these early stages and further confirm the random attachment, a liquid phase TEM (LP-TEM) technique was used to directly observe the particle formation in situ. FIGS. 16A-16F show sequential images depicting the formation of clusters of distorted nanorods, in which four distinct stages were identified. During the very early stage (t=0.63 min, FIG. 16A), many small gold NPs were formed. These particles increased in number and grew with time (t=7.0 min, FIG. 16B) before merging to form nanorods (t=9.7 min, second stage, FIG. 16C). Further particle attachment resulted in formation of distorted nanorods (t=10.5 min, third stage, FIG. 16D). Interestingly, these distorted nanorods randomly attached together (t=11.5 min, FIG. 16E) to form clusters (t=15 min, fourth stage, FIG. 16F) similar to those in FIGS. 9A-9D, indicating they are intermediates of coral-shaped particles. Unfortunately, direct observation of growth of these intermediates into the final spherical coral-shaped architecture using LP-TEM was unsuccessful, because, as they grew, the clusters fell out of the focal plane.

Based on these results, without wishing to be bound by a particular theory of operation, it is believed that random attachment of nanorods is due to Pep-1 binding onto the nanorod surfaces, and Pep-1 hydrophobicity and gold binding affinity are important factors in nanorod formation and attachment during spherical coral-shaped particle formation (FIG. 2).

Figure 19:
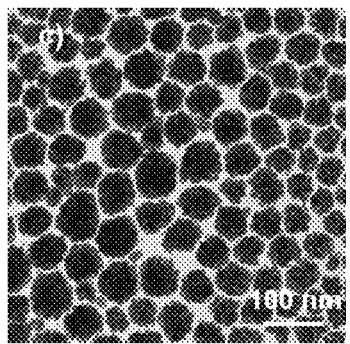
FIG. 19 is a TEM image showing nanoparticles of Pep-3/gold nanomaterial; scale bar, 100 nm.
Figure 20:
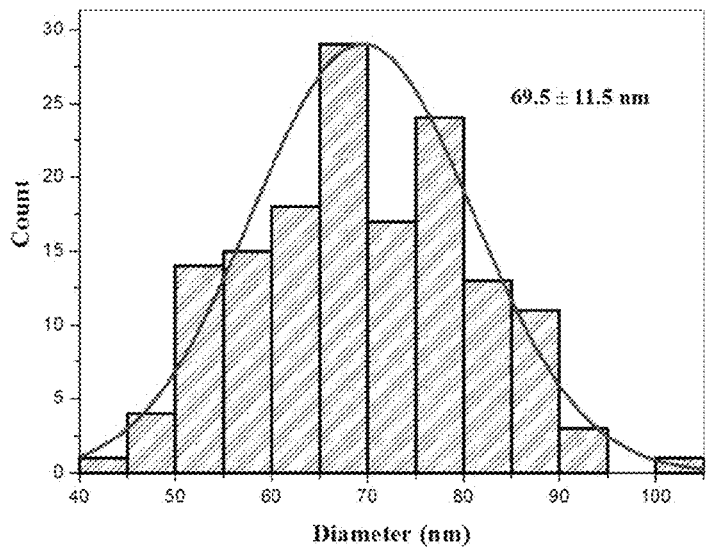
FIG. 20 is a graph showing the size distribution of the nanoparticles of FIG. 19.

To test the roles of Pep-1 hydrophobicity and binding affinity in the formation of spherical coral-shaped gold superstructures, two peptoids were synthesized by varying the number of Nce groups $(Nce)_n(Nab)_4(Ndc)_4$ (Pep-2, n=12; Pep-3, n=4) while maintaining the same hydrophobic domains. Because they have similar hydrophobicity, as evidenced by reverse phase UPLC, and the Nce group is a weak binder to the gold surface (Tan et al., *JACS* 2010, 132:5677-5686), it was reasoned that such variation would not disrupt the formation of coral-shaped nanoparticles. As expected, Pep-2 and Pep-3 both induced the formation of coral-shaped superstructures. FIGS. 17 and 18 show nanoparticles of the Pep-2/gold nanomaterial and the size distribution (62.6±14.48 nm). FIGS. 19 and 20 show nanoparticles of the Pep-3/gold nanomaterial and the size distribution (69.5±11.5 nm). Because Pep-1-Pep-3 all have the same hydrophobic domains $(Ndc)_4$, they are expected to exhibit similar hydrophobic interactions with gold nanomaterial surfaces. At pH 7.3, all the carboxyl groups are deprotonated and interact with gold surfaces through electronic interactions. While the influence of electronic interactions as a result of varying the number of carboxyl groups is minor for nanorod attachment, it is believed that the presence of hydrophobic interactions of $(Ndc)_4$ is important for the nanorod attachment, consistent with the hypothesis illustrated in FIG. 2.

Figure 21:
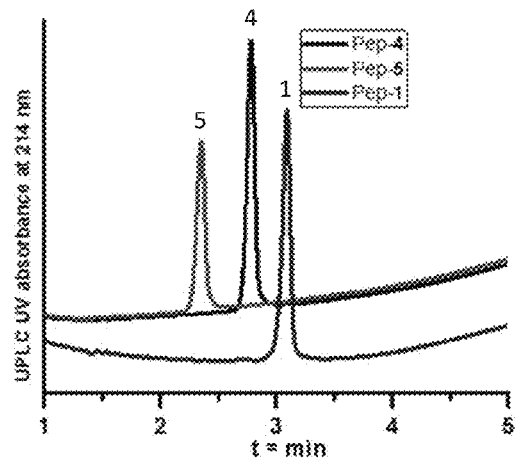
FIG. 21 is a graph showing relative hydrophobicity of Pep-1, Pep-4, and Pep-5 as determined by reverse phase UPLC.
Figure 23:
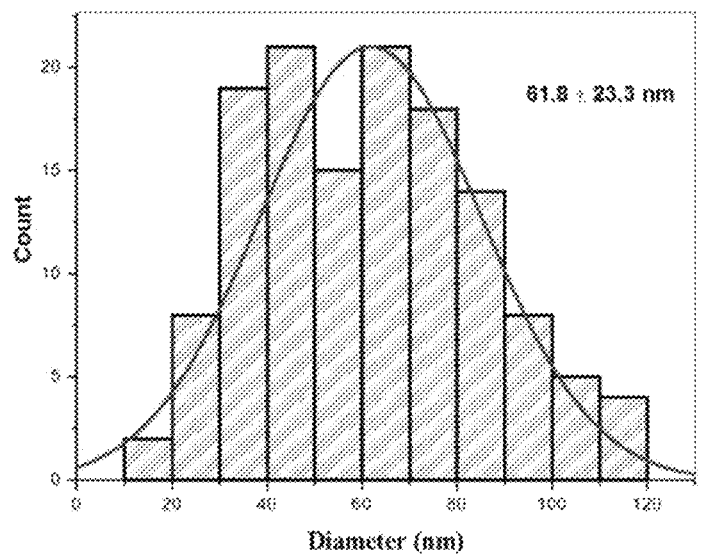
FIG. 23 is a graph showing the size distribution of the nanoparticles of FIGS. 22A-22B.
Figure 24A:
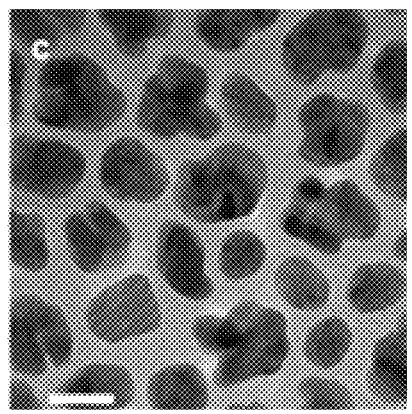
FIGS. 24A-24B are TEM images showing nanoparticles of Pep-5/gold nanomaterial; 24A scale bar=20 nm, 24B scale bar=25 nm.
Figure 24B:
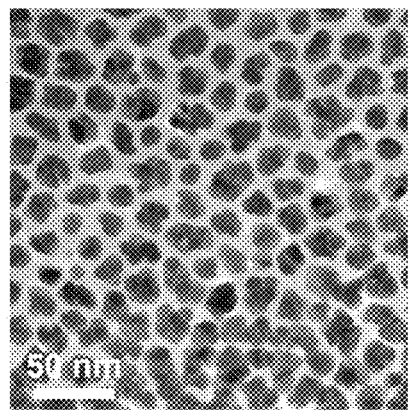

To further test the hypothesis, Pep-4 $((Nce)_8(Nab)_4(Nxpe)_4$ where X is Cl) and Pep-5 $((Nce)_8(Nab)_4(NXpe)_4$, where X is H) with varied substituent (X) of Nxpe groups were also synthesized. Pep-1, Pep-4 and Pep-5 exhibited tunable hydrophobicities in the order of Pep-1>Pep-4 (X=4-chloro)>Pep-5 (X=4-hydrogen). FIG. 21 is a graph showing relative hydrophobicity of the peptoids as determined by reverse phase UPLC (5-95% $CH_3CN$ in $H_2O$ at 0.4 mL/min over 5 min; detailed information provided under General Methods); the longer retention time indicates higher hydrophobicity. While Pep-4 induced formation of polydisperse coral-shaped particles (FIGS. 22A, 22B, 23) composed of nearly spherical building blocks having an average diameter of 61.8±23.3 nm, gold nanomaterials induced by Pep-5 exhibited an irregular architecture containing almost no nanorods (FIGS. 24A, 24B), indicating the hydrophobicity contributed from $(Ndc)_4$ groups of Pep-1 is important for nanorod formation and attachment during coral-shaped particle formation.

Figure 25A:
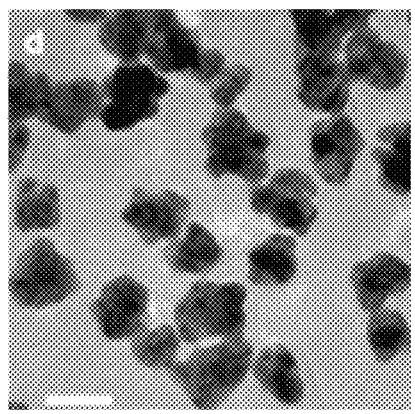
FIGS. 25A-25B are TEM images showing nanoparticles of Pep-6/gold nanomaterial; 25A scale bar=20 nm, 25B scale bar=25 nm.
Figure 25B:
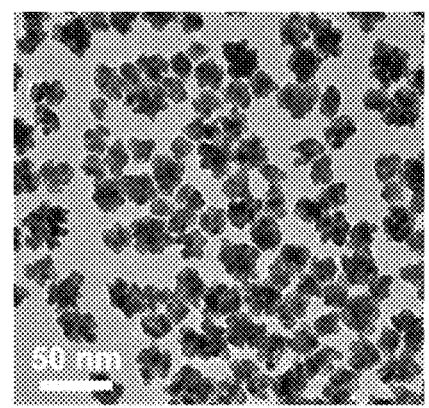

To test the significance of Nab residues in Pep-1, Pep-6 (a Pep-1 analogue without Nab groups—$(Nce)_8(Ndc)_4$) was used as a negative control. As shown in FIGS. 25A-25B, Pep-6 only induced formation of irregular particles, indicating Nab residues are important for Pep-1 binding to nanorods and their attachment during coral-shaped particle formation.

Example 3

Probing Interactions Between Peptoids and Gold

Figure 26A:
FIGS. 26A-26B are side and plan view images, respectively, showing representative structures of Pep-1 adsorbed at the aqueous Au(111) interface as predicted from REST-MD simulations; color code: C—cyan, O—red, N—blue, Cl—green, peptide backbone—purple; water molecules are not shown for clarity.
Figure 26B:
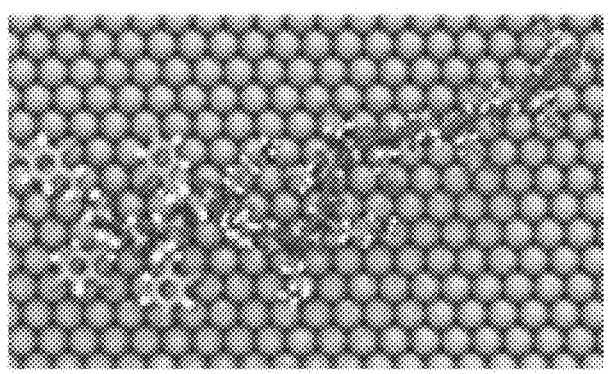
Figures 27A, 27B:
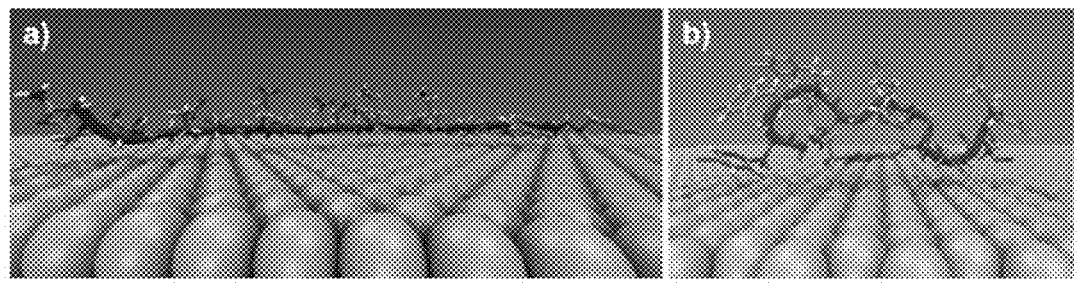
FIGS. 27A-27B are side view images showing representative structures of Pep-5 (27A) and Pep 6 (27B) adsorbed at the aqueous Au(111) interface as predicted from REST-MD simulations; color code: C—cyan, O—red, N—blue, Cl—green, peptide backbone—purple; water molecules are not shown for clarity.

To explore the underlying interactions that drive the observed behavior, Replica Exchange with Solute Tempering Molecular Dynamics (REST-MD) simulations (Wright et al., *Phys Chem Chem Phys* 2013, 15:4715-4726) were carried out to elucidate the links between peptoid sequence and binding behavior. Simulations of peptoids were done at the aqueous Au(111) interface to characterize peptoid-surface adsorption at the molecular level. (Details provided above.) Au(111) surfaces were used because Au(111) lattice fringes were observed in the nanorod building blocks (FIGS. 9A-9D). Furthermore, previous studies indicate that the Au(111) interface can provide a useful approximate structural model of more complex (i.e. poly-crystalline) Au interfaces under aqueous conditions when studying peptide/Au adsorption from solution (Bedford et al., *JACS* 2016, 138:540-548; Hughes et al., *Nanoscale* 2017, 9:421-432. Thus it was reasoned that REST-MD simulations of peptoids at the aqueous Au(111) interface could provide useful insight into the principal contact modes and conformational entropic contributions (vide infra) of peptoids adsorbed onto Au nanorod surfaces. In these simulations, a previously-established peptoid force field (Jim et al., *Nat Commun* 2016, 12252) was adapted and the peptoid-Au(111) interactions were predicted by modeling the adsorption of a single chain of each peptoid in contact with the aqueous Au(111) interface using the polarizable force-field GoIP-CHARMM (Wright et al., *J Chem Theory Comput* 2013, 9:1616-1630). Snapshots of a representative structure of Pep-1 (FIGS. 26A, 26B) reveal the close contact between the Ndc rings and the metal surface. Analogous images for Pep-5 and Pep-6 are provided in FIGS. 27A and 27B, respectively.

Figure 28:
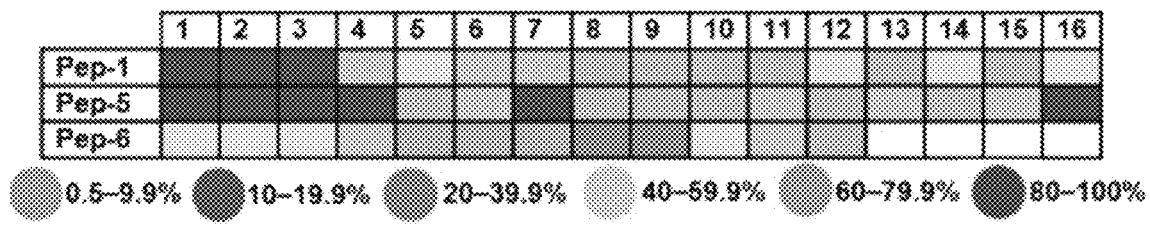
FIG. 28 is a table showing the average degree of peptoid-surface contact, on a residue-by-residue basis, predicted by REST-MD simulations for each of Pep-1, Pep-5, and Pep-6 adsorbed at the aqueous Au(111) interface; the side chain residues were numbered from the N- to C-termini.

The average degree of surface-peptoid contact for each residue (FIG. 28) showed that Pep-6 exhibited the weakest binding to Au(111) surfaces, confirming the significant contribution of Nab to Pep-1-gold binding. Multi-chain standard MD simulations of Pep-1 adsorbed on Au(111) (FIGS. 29, 30) further confirmed the importance of Nab. Specifically, Pep-1 amphiphilicity supported the substantive inter-peptoid electrostatic interactions between Nce and Nab side-chain groups.

Because both Pep-1 and Pep-5 exhibited almost an indistinguishable degree of contact with the Au(111) surfaces (FIG. 28), well-tempered metadynamics simulations (Barducci et al., *Phys Rev Lett* 2008, 100(2):020603) were further used to obtain the adsorption free energy of both dichlorobenzene (analogue of Ndc of Pep-1) and benzene (analogue of Nxpe of Pep-5) at the aqueous Au(111) interface. These simulations revealed a much stronger binding of dichlorobenzene (−33 kJ/mol; Pep-1 analogue) in contrast to that of benzene (−18 kJ/mol; Pep-5 analogue). Another factor that can affect binding affinity is conformational entropic contribution. For that, analysis of surface-adsorbed Pep-1 and Pep-5 was carried out using a clustering approach (see above for details) which yields the set of distinct, thermally-accessible conformations and their relative populations in the ensemble (Table 1). This analysis indicates a larger number of distinct thermally-accessible conformations of Pep-1 (43) compared to Pep-5 (20), suggesting the more favorable binding of Pep-1. Taken together, the simulation results indicate that Pep-1 binds to aqueous Au(111) interfaces much more strongly than does Pep-5.

TABLE 1

| Rank | Pep-1% | Pep-5% |
| --- | --- | --- |
| 1 | 45 | 53 |
| 2 | 17 | 14 |
| 3 | 10 | 14 |
| 4 | 5 | 9 |

TABLE 1-continued

| Rank | Pep-1% | Pep-5% |
|---|---|---|
| 5 | 5 | 3 |
| 6 | 4 | 3 |
| 7 | 3 | 2 |
| 8 | 2 | 1 |
| 9 | 1 | <1 |
| 10 | 1 | <1 |
| Total | 43 | 20 |

To experimentally confirm the above computational predictions, ToF-SIMS studies were conducted to investigate the binding affinities of Pep-1, Pep-5, and Pep-6 toward Au(111) surfaces in aqueous solutions. ToF-SIMS results showed that Pep-1 exhibits the strongest binding affinity, consistent with the computational predictions.

Freshly-cleaned Au(111) surfaces were incubated with Pep-1 (1.0 mM), 50% Pep-1 (0.5 mM) mixed with 50% Pep-5 (0.5 mM), 25% Pep-1 (0.25 mM) mixed with 75% Pep-5 (0.75 mM) and Pep-5 (1.0 mM). The distinct molecular ion of Pep-1 consisting of main peaks at m/z=2478.8, 2479.8, 2480.8, 2481.8, 2482.8, 2483.8, 2484.8, 2485.8, 2486.8, 2487.8, 2488.8, 2489.8 and 2490.8 was detected as long as Pep-1 was present in the incubation solution, whereas the molecular ions of Pep-5 consisting of five main peaks at m/z=2206.1, 2207.1, 2208.1, 2209.1, and 2210.1 were nearly undetectable no matter whether it was mixed with Pep-1 or not, demonstrating that Pep-1 exhibits significantly stronger adsorption onto Au(111) surfaces than Pep-5 does.

Freshly-cleaned Au(111) surfaces were incubated with $H_2O$, Pep-6 (1.0 mM) and 50% Pep-6 (0.5 mM) mixed with 50% Pep-1 (0.5 mM). In cases where Pep-6 existed in the solution with or without Pep-1, its molecular ion with main peaks at m/z=1966.4, 1967.4, 1968.4, 1969.4, 1970.4, 1971.4, 1972.4, 1973.4, 1973.4 and 1975.4 was not observed. It should be noted that the characteristic peak at m/z=1969.7 was assigned to $[Au_{10}]^+$ ion, which appeared on the spectra of all the three situations. In contrast, peaks of the molecular ion of Pep-1 were shown after Au(111) surface was incubated with the mixture of Pep-1 and Pep-6, verifying the stronger binding affinity of Pep-1 onto Au (111) surface than that of Pep-6.

Freshly-cleaned Au(111) surfaces were incubated with $H_2O$, Pep-3 (1.0 mM), and Pep-9 (1.0 mM). Pep-3 exhibited a significantly higher intensity of the observed molecular ion peaks at m/z=1963.6, 1964.6, 1965.6, 1966.6, 1967.6, 1968.6, 1969.6, 1970.6, 1971.6 and 1972.6 compared to Pep-9, indicating Pep-3 has higher binding affinity toward Au(111) than does Pep-9.

Example 4

Predictable Architecture of Hybrid Peptoid/Gold Nanomaterials

Figure 29:
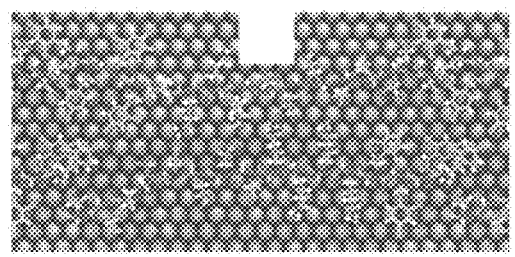
FIG. 29 is a two-chain plan view image showing two Pep-1 molecules with inter-peptoid contacts adsorbed at the aqueous Au(111) interface as predicted from REST-MD simulations; color code: C—cyan, O—red, N—blue, Cl—green, peptide backbone—purple; water molecules are not shown for clarity.
Figure 30:
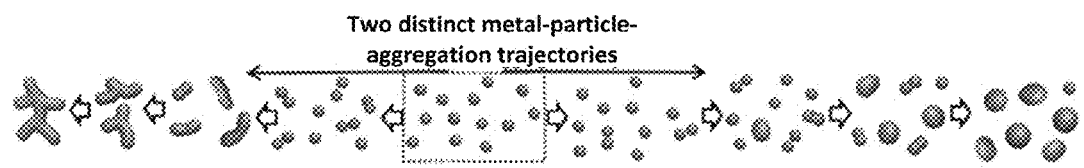
FIG. 30 is a schematic diagram illustrating two distinct, well-known metal-particle-aggregation trajectories.

Recent LP-TEM studies of metal NP suspensions have shown that particle interactions including slow aggregation and fast relaxation of metal NPs lead to fusion and formation of dumbbell structures that then relax back to spherical shapes, which minimizes the interfacial free energy (FIG. 30, right side) (Murphy et al., *Acc Chem Res* 2008, 41:1721-1739; Chen et al., *JACS* 2008, 130:13555-13557). On the other hand, numerous studies of metal thin film epitaxy (Cox et al., *Phy Rev B* 2005, 71:115414), as well as bulk solution studies (Habraken et al., *Nat Commun* 2013, 4:1507) have shown that when aggregation is rapid, but relaxation is slow, dendritic structures typical of diffusion-limited aggregation form instead. Moreover, the extended nature of these structures leads to enhanced particle capture and thus a smaller number of particles with a larger average size (FIG. 30, left side). Spherical coral-shaped particles present morphologies that are intermediates between these two end members. When aggregation and relaxation compete, partial relaxation leads to compact cores with dendritic arms that retain the history of nanoparticle attachment events. Therefore, it is reasonable to conclude that strong Pep-1-gold binding and peptoid amphiphilicity drive coral-shaped particle formation. The strong binding free energy of Pep-1 is directly correlated with low interfacial free energy and therefore low driving force for relaxation back to spherical particles. Moreover, the strong Pep-1-gold binding should reduce the mobility of surface atoms, thus further slowing the kinetics of relaxation, while the substantive inter-peptoid electrostatic interactions (FIG. 29) and the amphiphilicity of Pep-1 can be expected to lead to rapid particle aggregation.

Figure 31A:
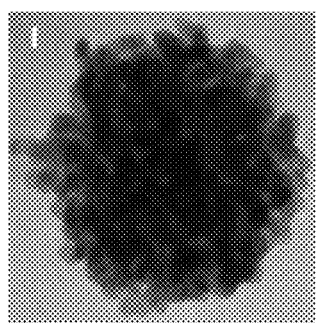
FIGS. 31A-31B are TEM images showing nanoparticles of Pep-7/gold nanomaterial; 31A scale bar=20 nm, 31B scale bar=100 nm.
Figure 31B:
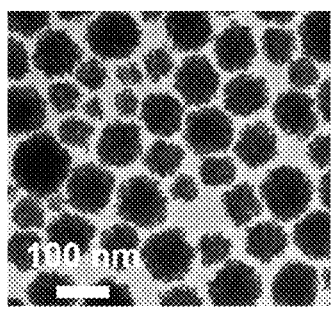
Figure 32:
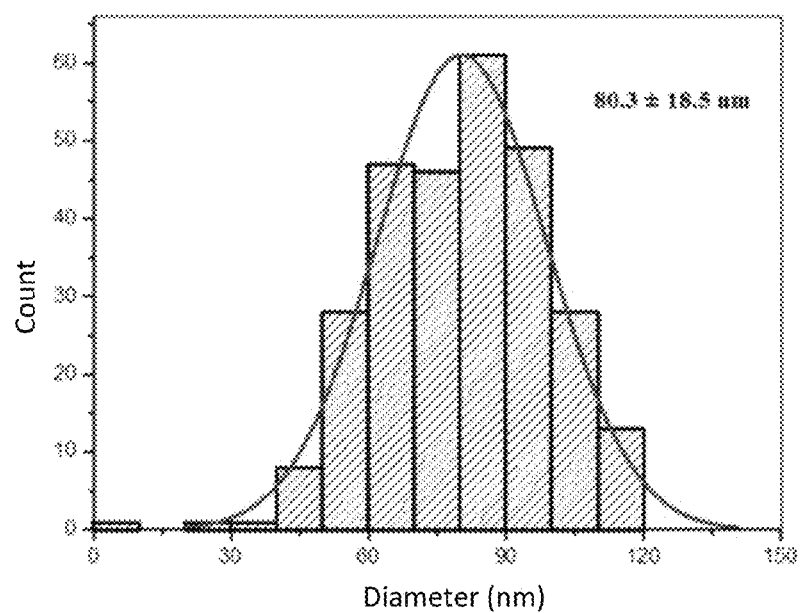
FIG. 32 is a graph showing the size distribution of the nanoparticles of FIGS. 31A-31B.
Figure 33A:
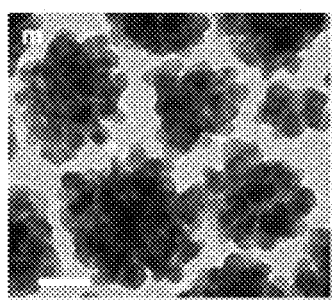
FIGS. 33A-33B are TEM images showing nanoparticles of Pep-8/gold nanomaterial; 33A scale bar=20 nm, 33B scale bar=100 nm.
Figure 33B:
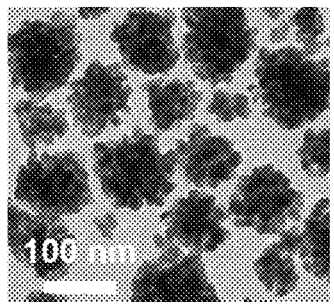
Figure 34:
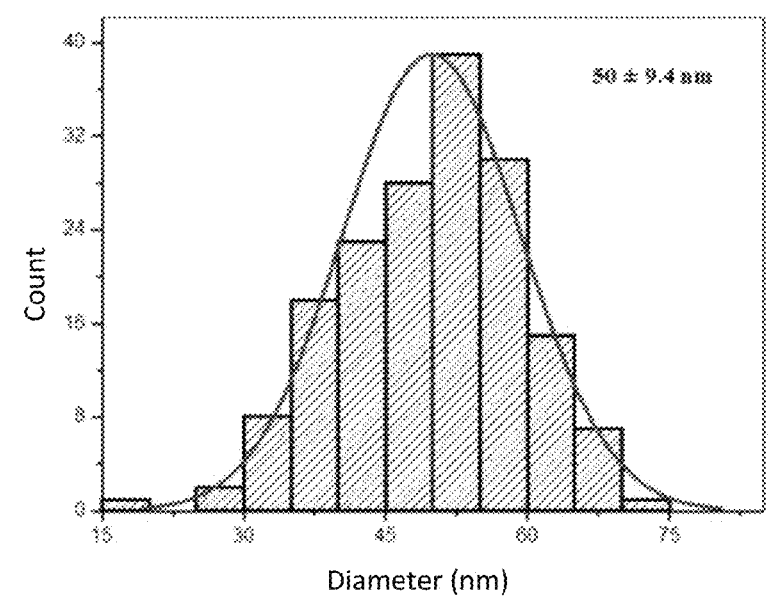
FIG. 34 is a graph showing the size distribution of the nanoparticles of FIGS. 33A-33B.

Based on the clear trends in particle architecture from spherical coral to irregular as the binding affinity or hydrophobicity of the peptoids decreases (FIGS. 21, 28), combined with the well-known metal-particle aggregation trajectories (FIG. 30), the following principles for peptoid design were deduced: For peptoids to induce coral-shaped nanoparticle formation they need adequate hydrophobicity and strong gold binding affinity; decreasing peptoid-gold binding affinity or providing inadequate hydrophobicity leads to a trend towards formation of spherical nanoparticles. To demonstrate these principles can be used to design peptoids that lead to predictive coral-shaped particle formation, two more peptoid sequences were designed in which $(Nab)_4$ was changed to $(Nae)_4$ (Pep-7) or $(Nab)_1$ (Pep-8), keeping the same number of Nce and Ndc groups, and a similar pattern and hydrophobicity compared to Pep-1. Therefore, a similar enhanced peptoid-gold binding affinity would be expected comparing to Pep-6 (a Pep-1 analogue without Nab). As expected, both Pep-7 (FIGS. 31A, 31B, 32) and Pep-8 (FIGS. 33A, 33B, 34) induced the formation of coral-shaped nanoparticles.

Figure 36:
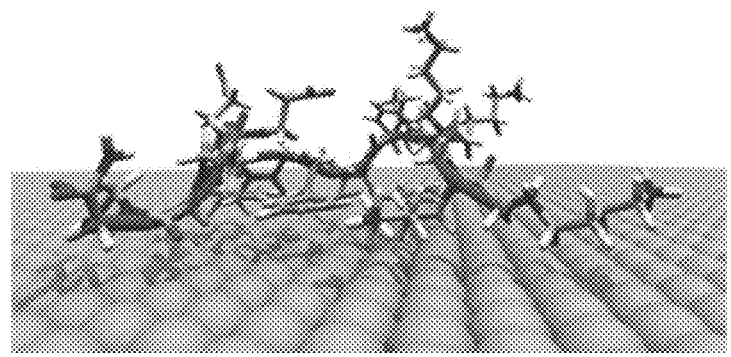
FIG. 36 is a representative structure of Pep-9 adsorbed at the aqueous Au(111) interface as predicted from REST-MD simulations; color code: C—cyan, O—red, N—blue, Cl—green, peptide backbone—purple; water molecules are not shown for clarity.
Figure 37:
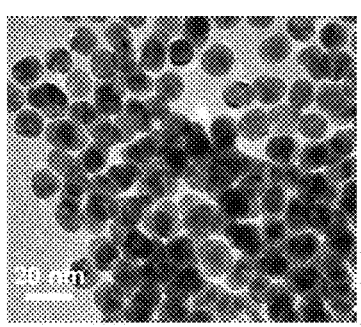
FIG. 37 is a TEM image showing nanoparticles of Pep-9/gold nanomaterial; scale bar=20 nm.
Figure 38:
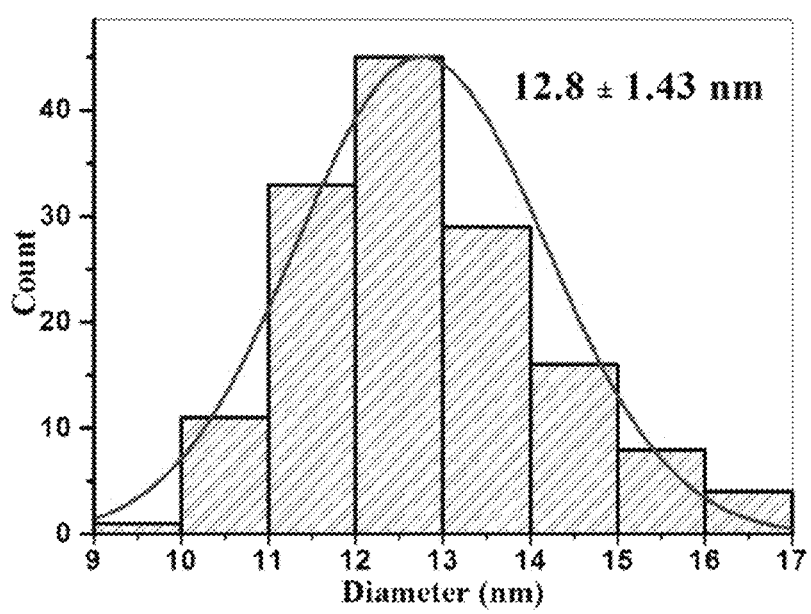
FIG. 38 is a graph showing the size distribution of the nanoparticles of FIG. 37.
Figure 39:
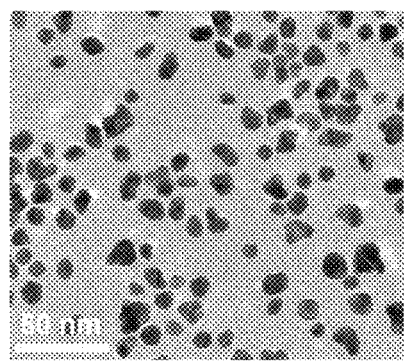
FIG. 39 is a TEM image showing nanoparticles of Pep-10/gold nanomaterial; scale bar=50 nm.
Figure 40:
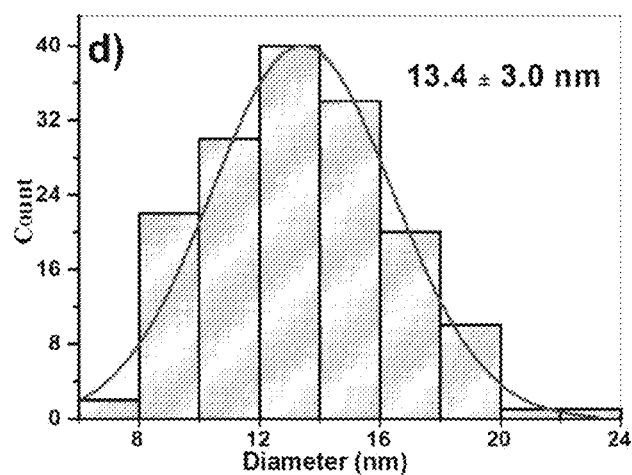
FIG. 40 is a graph showing the size distribution of the nanoparticles of FIG. 39.

As bio-controlled crystallization processes are sequence-dependent (Chen et al., *Angew Chem Int Ed* 2010, 49:1924-1942; Dickerson et al., *Chem Rev* 2008, 108:4935-4978), the arrangement of Nce, Ndc and Nab groups in Pep-1-Pep-3 was expected to be one of the key elements that determine the coral-shaped particle formation. To this end, Pep-9 $(Nce)_4(Ndc)_4(Nab)_4$ was synthesized, in which the four hydrophobic monomers of Ndc in Pep-3 were moved from the N-terminus to the middle positions. Compared to Pep-3, its analogue Pep-9 exhibited lowered gold binding affinity as evidenced by TOF-SIMS results (not shown) and simulation results (FIGS. 35, 36), where the Pep-9-surface contact was similar to that of Pep-6 (FIG. 28) but with the Ndc/Nce blocks swapped). As expected, Pep-9 induced the formation of monodisperse and nearly spherical NPs (FIGS. 37, 38). Similar results were observed when a Pep-2 analogue, namely Pep-10 $(Nce)_{12}(Ndc)_4(Nab)_4$, was used (FIGS. 39, 40).

To investigate the influence of the protonation state of peptoids in spherical coral-shaped nanoparticle formation, the reaction condition at pH 5.5 was evaluated. According to the titration curve of Pep-1, Nce groups will start to become protonated. The X-ray photoelectron spectroscopy (XPS) measurements (Table 2) showed that the binding affinity of Pep-1 toward Au(111) lowered from pH 7.3 to pH 5.5.

TABLE 2

| | The average Cl concentration | $Cl_{2p}/Au_{4f}$ |
|---|---|---|
| Pep-1 at pH 5.5 (1.0 mM) | 3.5 AT % ± 0.17 | 0.10 |
| Pep-1 at pH 7.3 (1.0 mM) | 4.0 AT % ± 0.13 | 0.113 |

AT = atomic percent

Figure 35:
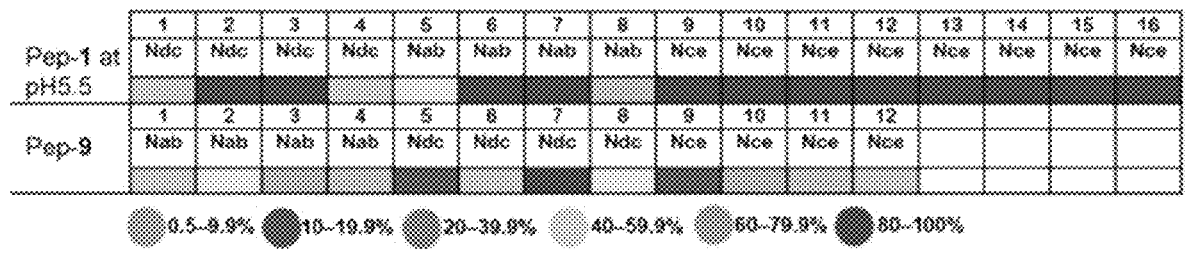
FIG. 35 is a table showing the average degree of peptoid-surface contact, on a residue-by-residue basis, predicted by REST-MD simulations for each of Pep-1 at pH 5.5 and Pep-9 adsorbed at the aqueous Au(111) interface; the side chain residues were numbered from the N- to C-termini.
Figure 41:
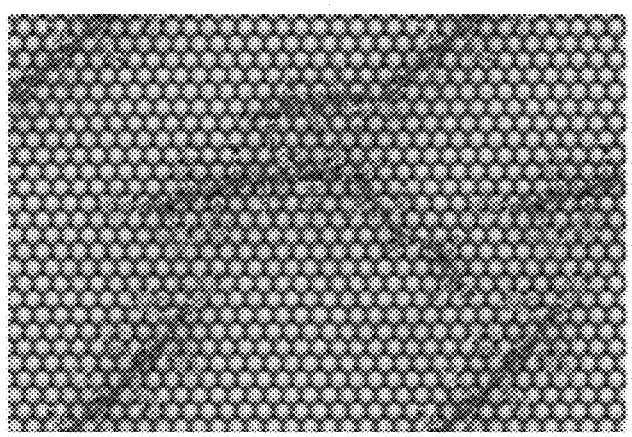
FIG. 41 is a two-chain plan view of Pep-1 at pH 5.5, indicating the lack of favorable inter-peptoid contacts; color code: C—cyan, O—red, N—blue, Cl—green, peptide backbone—purple; water molecules are not shown for clarity.
Figure 43:
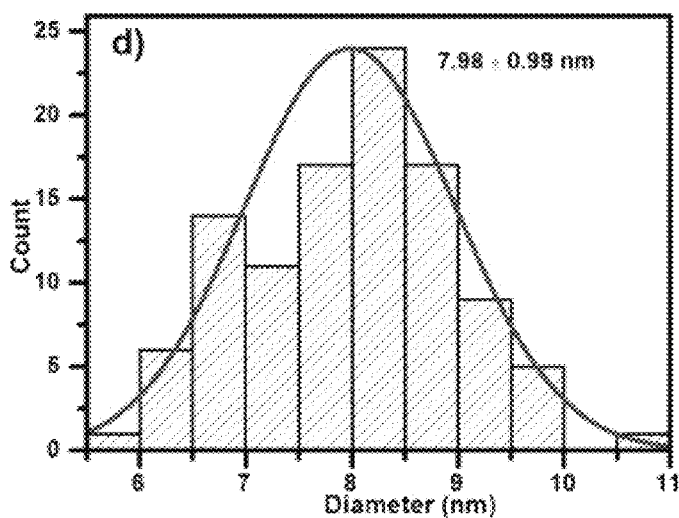
FIG. 43 is a graph showing the size distribution of the nanoparticles of FIGS. 42A, 42B.

REST-MD simulation results indicated that a single-chain of Pep-1 at pH 5.5 (where all Nce groups were protonated) yielded a comparable degree of contact with Au(111) relative to Pep-1 at pH 7.3 (FIG. 35). However, multi-chain MD simulations of Pep-1 at pH5.5 revealed a dramatic reduction in inter-peptoid interactions (FIG. 41) and a loss of the tightly-packed, amphiphilically-driven anti-parallel chain arrangement compared with Pep-1 at pH 7.3 (FIG. 29). As expected, at pH 5.5, Pep-1 induced the formation of nearly spherical nanoparticles (FIGS. 42A, 42B, 43).

Example 5

Plasmonic Properties of Dendritic Gold Nanomaterials

Figure 44:
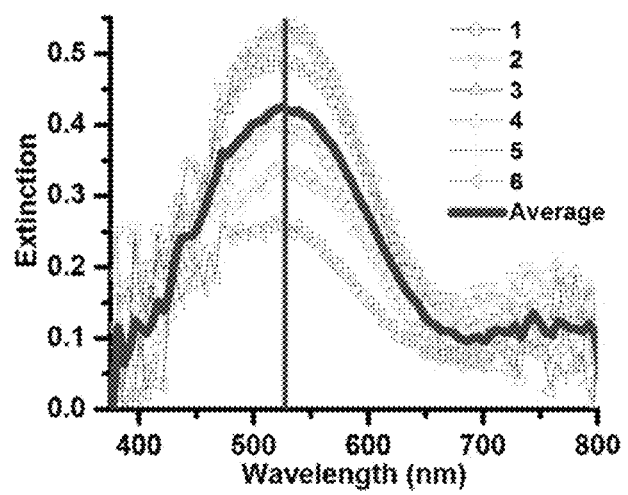
FIG. 44 is a graph showing the hyperspectral UV-Vis extinction of six individual particles of Pep-1/gold nanomaterial.
Figure 45:
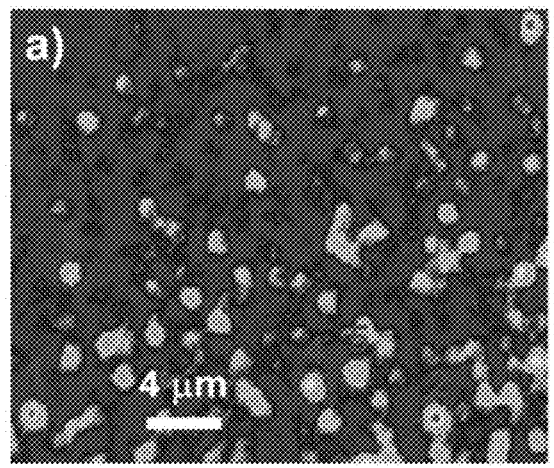
FIG. 45 is a hyperspectral UV-Vis extinction microscope image showing the six Pep-1/gold particles of FIG. 44; scale bar=4 µm.
Figure 46:
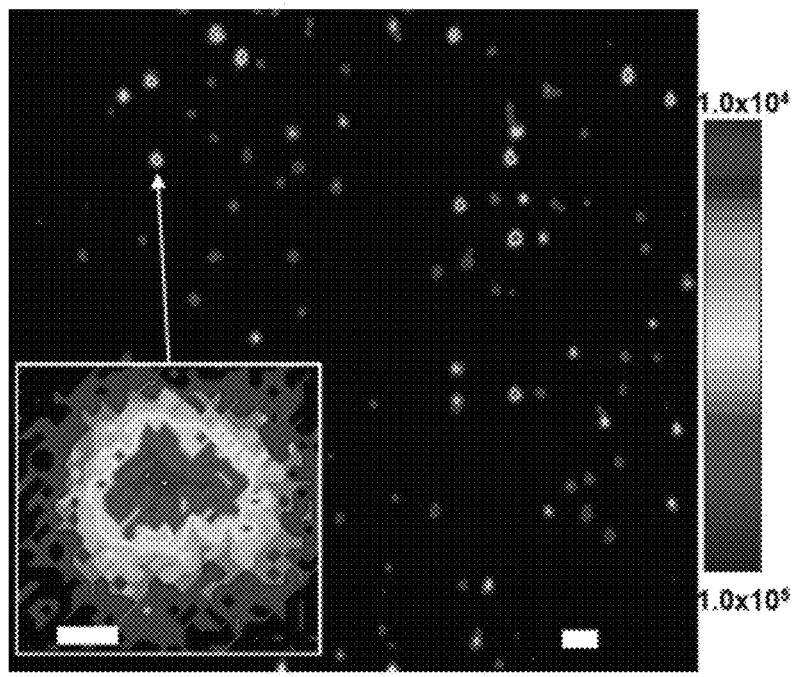
FIG. 46 is a three-photon photoemission electron micrograph (TP-PEEM) of a sparse distribution of particles showing the photoemission enhancement map (scale bar=50 nm) in which a single coral-shaped Pep-1/gold nanoparticle (insert; scale bar=20 nm) exhibited a plasmonic enhancement as high as $10^5$.
Figure 47:
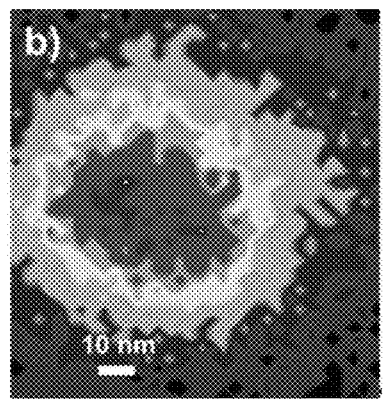
FIG. 47 is a near-field enhancement map from a single isolated coral-shaped particle from a high-resolution TP-PEEM.

To evaluate the plasmonic properties of the Pep-1-induced coral-shaped gold nanoparticles, a combination of hyperspectral UV-Vis extinction microscopy and TP-PEEM was employed (details provided above). Whereas the former reports on the plasmonic response of a single particle, the latter can be used to map the local electric fields generated from spherical coral-shaped nanoparticles with nanometer resolution. Spectra were obtained by averaging over a total of 9 pixels (130 nm$^2$/pixel) centered on each particle. As shown in FIGS. 44 and 45, these coral-shaped nanoparticles exhibit a well-defined plasmon resonance centered at 528 nm, indicating the uniformity of their plasmonic responses. The enhancement images (FIGS. 46 and 47) reveal that individual coral-shaped particles support a plasmonic enhancement factor of as high as 10$^5$, which is 2-3 orders of magnitude stronger than those achieved from Pep-5-induced Au NPs (FIG. 48) and other previously reported plasmonic NPs (Peppernick et al., *J Chem Phys* 2011, 134:034507; Ruan et al., *ACS Nano* 2014, 8:6934-6944). These data confirm that the unique plasmonic enhancement arises from the coral-shaped architecture. High-resolution TP-PEEM data (FIGS. 46, 47) reveal that the coral-shaped particle center comprises the most pronounced region of plasmonic enhancement, consistent with our proposed model of a spherical coral-shaped particle (FIG. 2).

Example 6

Preparation and Characterization of Pt- and/or Pd-Based Nanomaterials

Lyophilized peptoids (3.0×10$^{-6}$ mol) were mixed with 1.5 mL ultrapure water in glass vial, and 10 µL saturated $(NH_4)_2CO_3$ solutions were used to facilitate dissolution. The final concentration of peptoid stock solution was 2.0 mM.

Method 1: 75 µL of 2 mM Pep-1, 30 µL of 0.2 M ascorbic acid (AA) solution, 250 µL of 0.2 M HEPES solution were added into 145 µL of water. 6.0 µL of $K_2PtCl_4$ (0.1 M) was then added, vortexed, and left undisturbed at room temperature. After 6 hours, the solution were heated to 35° C. After 24 hours, Pt nanomaterials were formed.

Method 2: 25 µL of 2 mM Pep-1 and 30 µL of 0.2 M AA solution were added into 445 µL of water. 6.0 µL of $K_2PtCl_4$ or $Na_2PdCl_4$ (0.1 M) was then added and vortexed. The solution was kept at 35° C. After 24 hours, Pt or Pd nanomaterials were formed.

The centrifuged and purified Pt or Pd nanomaterials were incubated at 60° C. for 30 h in aqueous solution, and then used for TEM studies.

Pep-1 induced the formation of both spherical coral-shaped Pt- and Pd-nanoparticles (FIGS. 49A-B, 50A-B, 51A-B). Similarly, these Pt- and Pd-coral-shaped particles are highly stable and remained intact after being exposed to 60° C. in water for 30 h. Taken together, these results demonstrate that embodiments of the disclosed method provide a level of predictability and control in the synthesis of metallic coral-shaped particles that previously reported approaches, including templating mechanisms, do not offer (Chen et al., *Angew Chem Int Ed* 2010, 49:1924-1942; Dickerson et al., *Chem Rev* 2008, 108:4935-4978; Meldrum et al., *chem Rev* 2008, 108:4332-4432; Chiu et al., *Chem Soc Rev* 2013, 42:2512-2527; Slocik et al., *Curr Opin Biotechnol* 2017, 46:7-13).

Example 7

Preparation and Characterization of POS-Based Nanomaterials

Pep-11, $(Nce)_8(Nab)_4(Nxpe)_4$ where X is Br, was combined with polyhedral oligomeric silsesquioxane nanoclusters to form POSS/Pep-11:

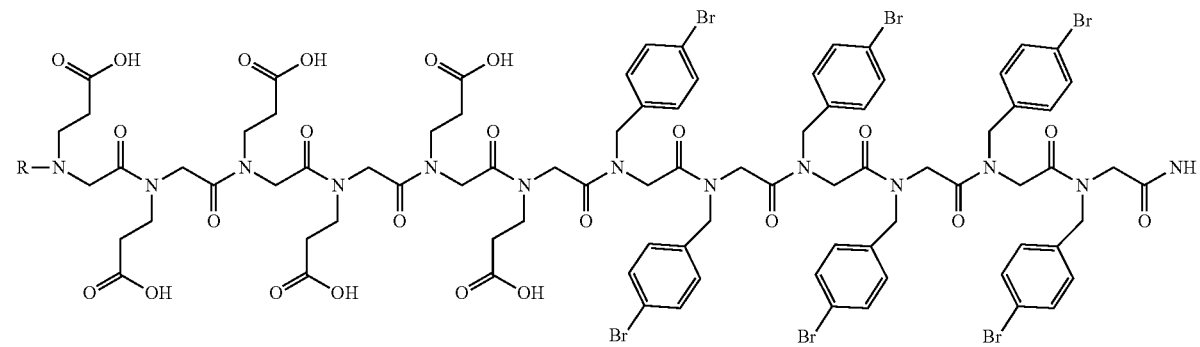

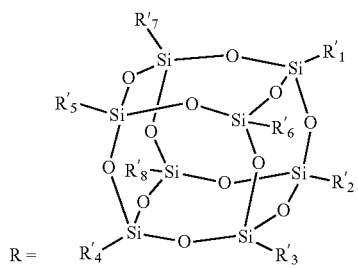

R = where R'₁ and R'₃-R'₈ are isobutyl and R'₂ is (CH₂)₃N(H)CH₂C(O)-.

The POS/Pep-11 constructs assembled into vesicle-like hybrid materials (FIG. 52). Co-assembly of additional Pep-11 with the POS/Pep-11 constructs at a 2:1 molar ratio led to the formation of highly ordered nanotubes (FIG. 53).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A method, comprising:
 producing a hybrid material by:
  combining a plurality of peptoids, each peptoid comprising a sequence of N-substituted glycine residues and comprising at least one carboxyl- and at least one amino-containing side chain, and an inorganic material comprising metal cations with a solvent to provide a solution;
  adding a reducing agent to the solution, and
  allowing a reaction to occur for a period of time effective to provide reduction of the cations to form nanoparticles, subsequent merging of nanoparticles to form larger particles, adsorption of at least some of the plurality of peptoids to surfaces of the particles, and random attachment of particles to each other via peptoid-peptoid and peptoid-surface interactions, thereby forming the hybrid material,
  wherein the sequence of N-substituted glycine residues comprises residues selected from N-(2-carboxyethyl)glycine (Nce), N-(4-aminobutyl)glycine (Nab), N-[2-(4-X-phenyl)ethyl]glycine (Nxpe) where X is H or chloro, N-[2-(2,4-dichlorophenyl)ethyl]glycine (Ndc), N-(4-aminoethyl)glycine (Nae), or any combination thereof.

2. The method of claim 1, wherein the sequence of N-substituted glycine residues comprises a group of at least four Ndc residues, and the larger particles formed by the subsequent merging of nanoparticles comprise distorted nanorods.

3. The method of claim 1, wherein the sequence of N-substituted glycine residues further comprises:
 at least one hydrophobic side chain.

4. The method of claim 1, wherein the plurality of peptoids comprises:

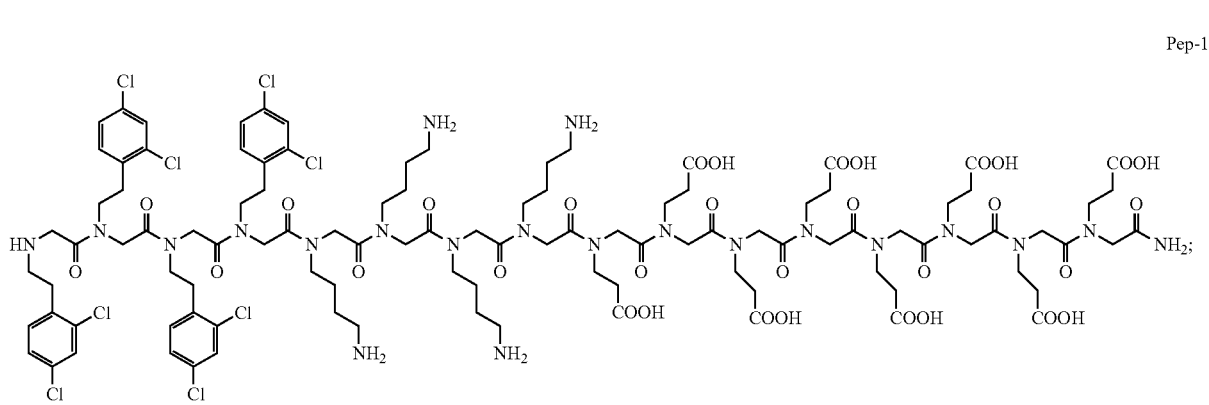

Pep-1

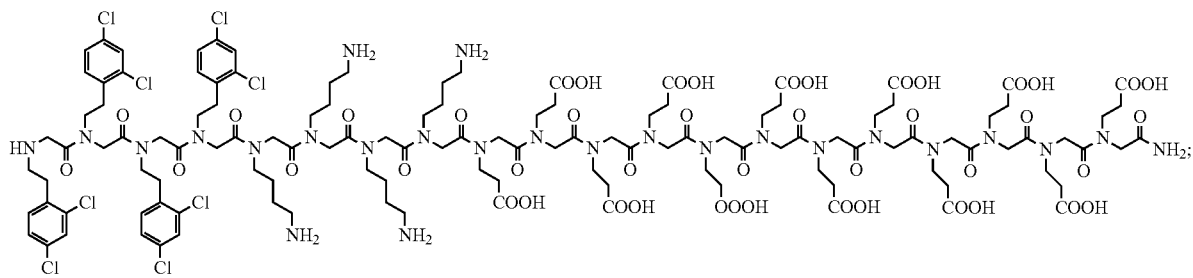

Pep-2

Pep-3
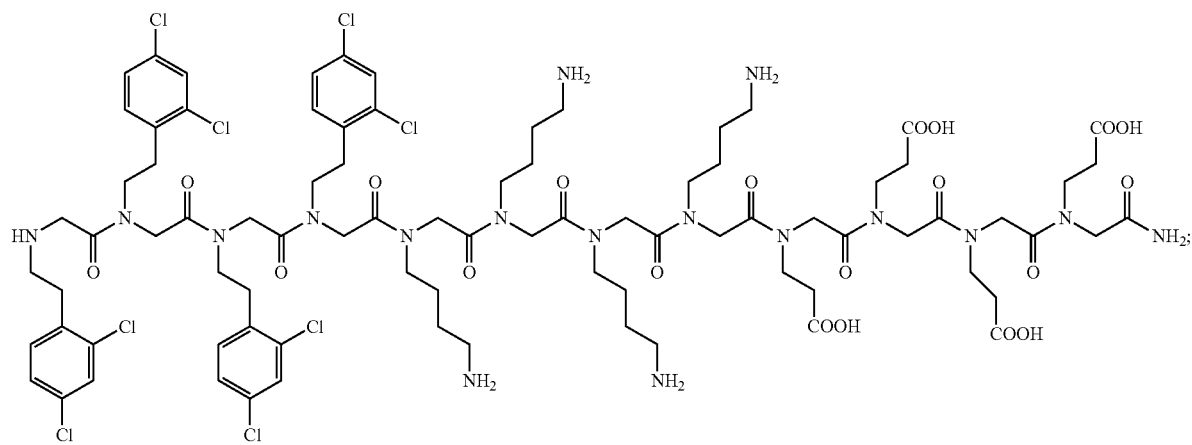
Pep-4
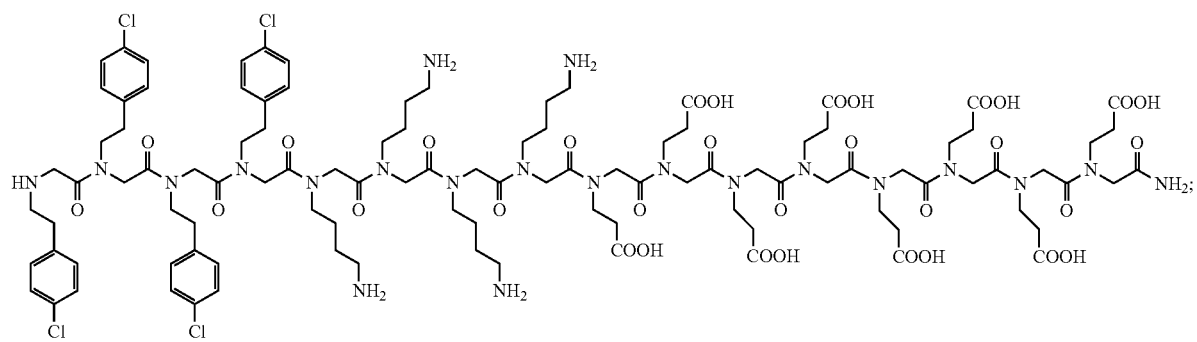
Pep-7
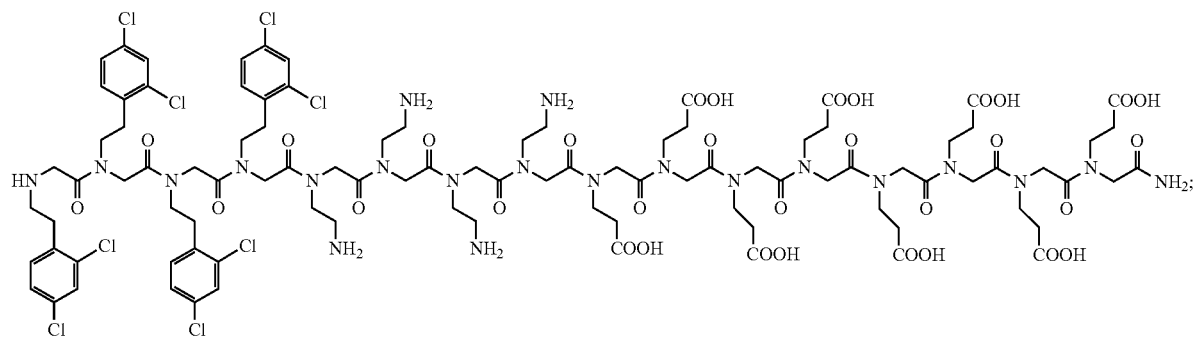
Pep-8
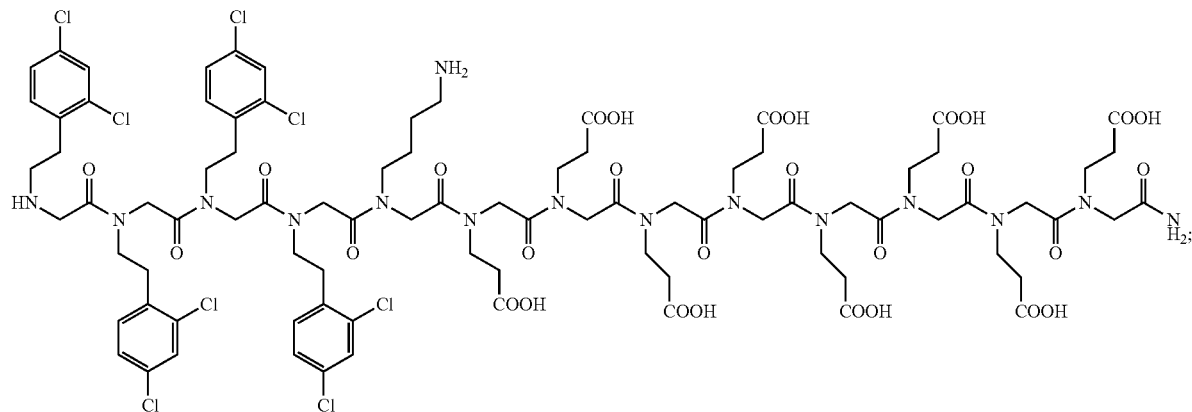

-continued

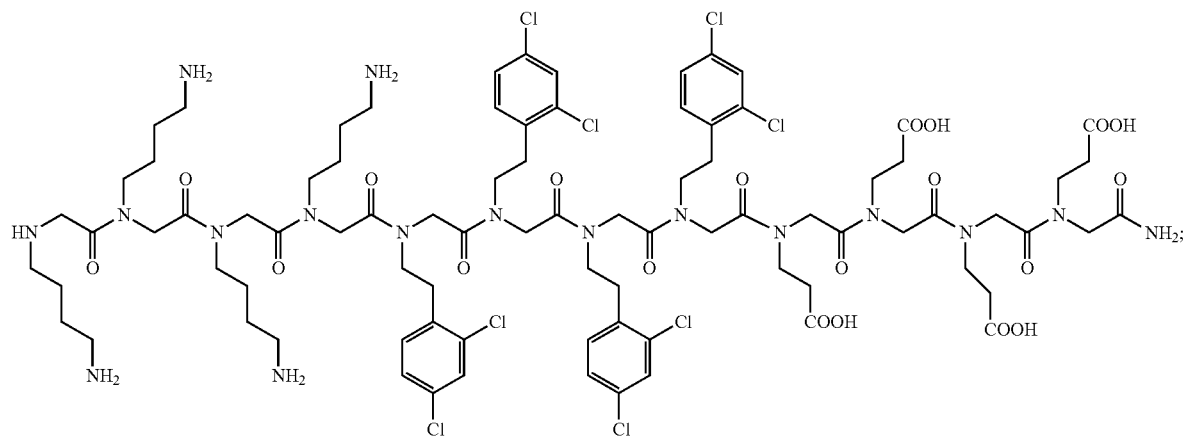

Pep-9

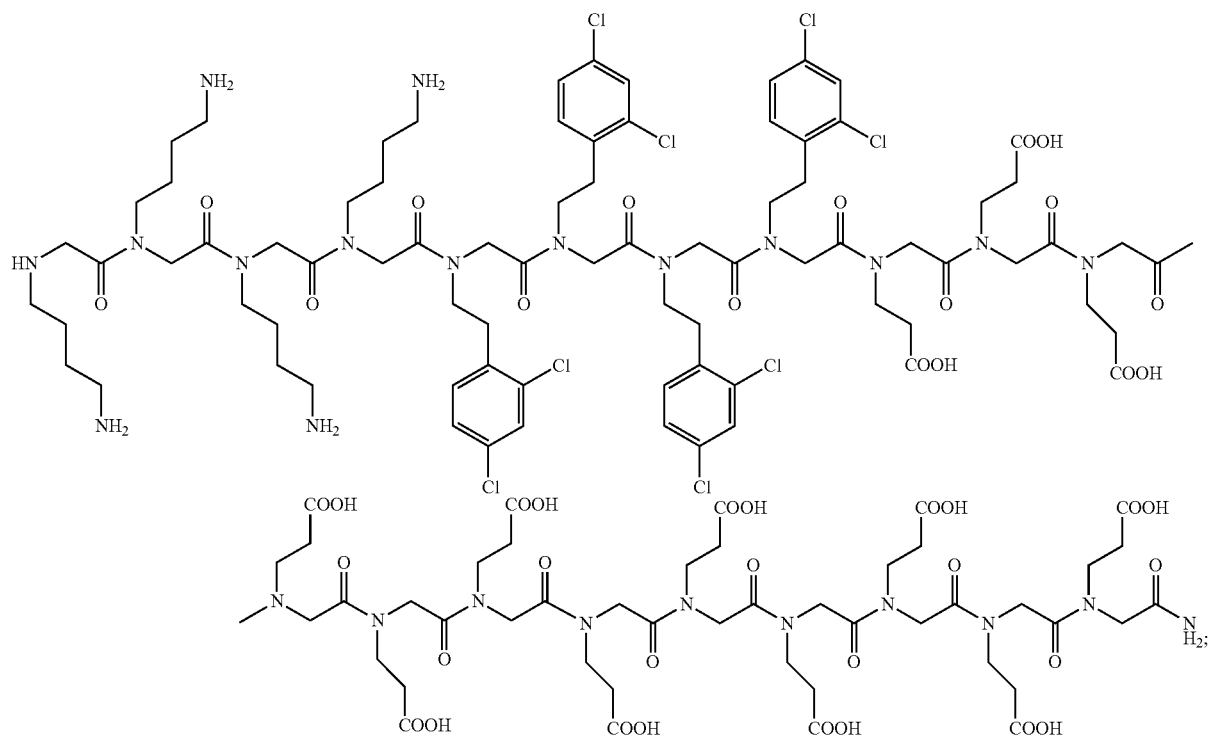

Pep-10 or any combination thereof.

5. The method of claim 1, wherein the inorganic material comprises Au, Pd, Pt, Ag, or any combination thereof.

6. The method of claim 5, wherein:

the plurality of peptoids comprises Pep-1, Pep-2, Pep-3, Pep-4, Pep-7, or Pep-8; and the hybrid material has a dendritic or spherical dendritic architecture.

7. The method of claim 2, wherein nanorod clusters are formed by subsequent adsorption of additional peptoids of the plurality of peptoids to surfaces of the distorted nanorods and random attachment of distorted nanorods to each other by peptoid-peptoid and peptoid-surface interactions.

8. The method of claim 1, wherein:

the reducing agent comprises 4-(2-hydroxyethyl)-1-piperazineethanesulfonic acid, ascorbic acid or a combination thereof; and the inorganic material comprising metal cations comprises chloroauric acid, potassium tetrachloroplatinate (II), sodium tetrachloropalladate (II), or a combination thereof.

9. The method of claim 1, wherein:

the sequence of N-substituted glycine residues includes a plurality of Ndc residues in a mid-portion of the sequence;

the sequence of N-substituted glycine residues does not comprise terminal Ndc residues; and the hybrid material has a spherical architecture.

10. The method of claim 1, wherein the inorganic material comprises Au, Pt, Pd, or a combination thereof, and the sequence of N-substituted glycine residues comprises one or more Ndc residues.

11. The method of claim 1, wherein the inorganic material comprises Ag, and the sequence of N-substituted glycine residues comprises one or more Nce residues.

12. The method of claim 1, wherein:

the inorganic material comprises Au, Pt, Pd, or a combination thereof;

the sequence of N-substituted glycine residues comprises (i) a group of at least three terminal Ndc residues and (ii) Nab and Nce residues; and the hybrid material has a spherical dendritic architecture.

13. The method of claim 12, wherein the sequence of N-substituted glycine residues comprises:

a group of at least four terminal Ndc residues;

one or more groups of Nab residues, each group including 4-12 residues; and one or more groups of Nce residues, each group including 4-12 residues.

14. A method, comprising:

producing a hybrid material having an architecture by:
combining a plurality of peptoids, each peptoid comprising a sequence of N-substituted glycine residues and an inorganic material comprising cations with a solvent to provide a solution;
adding a reducing agent to the solution, and
allowing a reaction to occur for a period of time effective to provide reduction of the cations to form nanoparticles, subsequent merging of nanoparticles to form larger particles, adsorption of at least some of the plurality of peptoids to surfaces of the particles, and random attachment of particles to each other via peptoid-peptoid and peptoid-surface interactions, thereby forming the hybrid material, the hybrid material having an architecture based at least in part on the sequence, wherein the inorganic material comprising cations comprises chloroauric acid, potassium tetrachloroplatinate (II), sodium tetrachloropalladate (II), or a combination thereof, the plurality of peptoids comprises Pep-1, Pep-2, Pep-3, Pep-4 Pep-7, or Pep-8, and the architecture is dendritic or spherical dendritic.

* * * * *